(12) United States Patent
Worrell et al.

(10) Patent No.: US 9,872,725 B2
(45) Date of Patent: Jan. 23, 2018

(54) RF TISSUE SEALER WITH MODE SELECTION

(71) Applicant: Ethicon Endo-Surgery, LLC, Guaynabo, PR (US)

(72) Inventors: Barry C. Worrell, Centerville, OH (US); Charles J. Scheib, Loveland, OH (US); Benjamin D. Dickerson, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 241 days.

(21) Appl. No.: 14/700,050

(22) Filed: Apr. 29, 2015

(65) Prior Publication Data

US 2016/0317215 A1    Nov. 3, 2016

(51) Int. Cl.
*A61B 18/14* (2006.01)
*A61B 18/00* (2006.01)

(52) U.S. Cl.
CPC ...... *A61B 18/1445* (2013.01); *A61B 18/1482* (2013.01); *A61B 2018/0063* (2013.01);
(Continued)

(58) Field of Classification Search
CPC ............ A61B 18/1445; A61B 18/1482; A61B 2018/00184; A61B 2018/00601;
(Continued)

(56) References Cited

U.S. PATENT DOCUMENTS 2,366,274 A   1/1945 Luth et al.
2,458,152 A   1/1949 Eakins
(Continued)

FOREIGN PATENT DOCUMENTS

CN    2868227 Y    2/2007
CN    102834069 A  12/2012
(Continued)

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
(Continued)

*Primary Examiner* — Michael Peffley

(57) ABSTRACT

Aspects of the present disclosure are presented for a surgical instrument for cutting and sealing tissue with a mode selection assembly. The mode selection assembly allows for a user to safely activate or disable a cutting functionality and a sealing functionality through use of electrosurgical energy. In some embodiments, the mode selection assembly allows for a more automated application of the electrosurgical energy and the cutting functionality when applied to a surgical site. The mode selection assembly may also include a knob configured to switch between the aforementioned settings. Various control mechanisms are also disclosed to lock and unlock the cutting element, such as a motorized locking mechanism, a solenoid locking mechanism, a mechanical mechanism and use of a nitinol wire. The inclusion of the mode selection assembly allows for a user to more safely utilize the surgical instrument by intentionally disabling functionality that may otherwise be inadvertently activated.

20 Claims, 17 Drawing Sheets

(52) U.S. Cl.
CPC ............... *A61B 2018/00184* (2013.01); *A61B 2018/00601* (2013.01); *A61B 2018/00916* (2013.01); *A61B 2018/00958* (2013.01); *A61B 2018/1455* (2013.01)

(58) Field of Classification Search
CPC .. A61B 2018/0063; A61B 2018/00916; A61B 2018/00958; A61B 2018/1455
See application file for complete search history.

(56) References Cited

U.S. PATENT DOCUMENTS

| | | |
|---|---|---|
| 2,510,693 A | 6/1950 | Green |
| 2,867,039 A | 1/1959 | Zach |
| 3,166,971 A | 1/1965 | Stoecker |
| 3,525,912 A | 8/1970 | Wallin |
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,203,430 A | 5/1980 | Takahashi |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,314,559 A | 2/1982 | Allen |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,880,015 A | 11/1989 | Nierman |
| 4,910,389 A | 3/1990 | Sherman et al. |
| 4,920,978 A | 5/1990 | Colvin |
| 4,936,842 A | 6/1990 | D'Amelio et al. |
| 5,020,514 A | 6/1991 | Heckele |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,312,023 A | 5/1994 | Green et al. |
| 5,318,563 A | 6/1994 | Malis et al. |
| 5,318,564 A | 6/1994 | Eggers |
| 5,318,589 A | 6/1994 | Lichtman |
| 5,326,013 A | 7/1994 | Green et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,456,684 A | 10/1995 | Schmidt et al. |
| 5,458,598 A * | 10/1995 | Feinberg ............ A61B 18/1445 606/205 |
| 5,465,895 A | 11/1995 | Knodel et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,681 A | 7/1996 | Strul et al. |
| 5,542,916 A | 8/1996 | Hirsch et al. |
| 5,558,671 A | 9/1996 | Yates |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,607,450 A | 3/1997 | Zvenyatsky et al. |
| 5,611,813 A | 3/1997 | Lichtman |
| 5,618,307 A | 4/1997 | Donlon et al. |
| 5,624,452 A | 4/1997 | Yates |
| 5,632,432 A | 5/1997 | Schulze et al. |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman |
| 5,836,909 A | 11/1998 | Cosmescu |

(56) References Cited

U.S. PATENT DOCUMENTS

| | | |
|---|---|---|
| 5,836,943 A | 11/1998 | Miller, III |
| 5,836,990 A | 11/1998 | Li |
| 5,853,412 A | 12/1998 | Mayenberger |
| 5,876,401 A | 3/1999 | Schulze et al. |
| 5,878,193 A | 3/1999 | Wang et al. |
| 5,880,668 A | 3/1999 | Hall |
| 5,891,142 A | 4/1999 | Eggers et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| H1904 H | 10/2000 | Yates et al. |
| 6,132,368 A | 10/2000 | Cooper |
| 6,144,402 A | 11/2000 | Norsworthy et al. |
| 6,152,923 A | 11/2000 | Ryan |
| 6,154,198 A | 11/2000 | Rosenberg |
| 6,162,208 A | 12/2000 | Hipps |
| 6,174,309 B1 | 1/2001 | Wrublewski et al. |
| 6,176,857 B1 | 1/2001 | Ashley |
| 6,190,386 B1 | 2/2001 | Rydell |
| 6,206,876 B1 | 3/2001 | Levine et al. |
| 6,228,080 B1 | 5/2001 | Gines |
| 6,231,565 B1 | 5/2001 | Tovey et al. |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,364,888 B1 | 4/2002 | Niemeyer et al. |
| 6,387,109 B1 | 5/2002 | Davison et al. |
| 6,391,026 B1 | 5/2002 | Hung et al. |
| 6,398,779 B1 | 6/2002 | Buysse et al. |
| 6,409,722 B1 | 6/2002 | Hoey et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,689 B1 | 10/2002 | Qin et al. |
| 6,464,702 B2 | 10/2002 | Schulze et al. |
| 6,480,796 B2 | 11/2002 | Wiener |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,551,309 B1 | 4/2003 | LePivert |
| 6,554,829 B2 | 4/2003 | Schulze et al. |
| 6,558,376 B2 | 5/2003 | Bishop |
| 6,562,037 B2 | 5/2003 | Paton et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,610,060 B2 | 8/2003 | Mulier et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,644,532 B2 | 11/2003 | Green et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,673,248 B2 | 1/2004 | Chowdhury |
| 6,679,882 B1 * | 1/2004 | Kornerup ........... A61B 18/1445 606/46 |
| 6,682,501 B1 | 1/2004 | Nelson et al. |
| 6,695,840 B2 | 2/2004 | Schulze |
| 6,722,552 B2 | 4/2004 | Fenton, Jr. |
| 6,733,498 B2 | 5/2004 | Paton et al. |
| 6,746,443 B1 | 6/2004 | Morley et al. |
| 6,752,815 B2 | 6/2004 | Beaupre |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,783,524 B2 | 8/2004 | Anderson et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 6,977,495 B2 | 12/2005 | Donofrio |
| 6,994,709 B2 | 2/2006 | Iida |
| 7,000,818 B2 | 2/2006 | Shelton, IV et al. |
| 7,001,382 B2 * | 2/2006 | Gallo, Sr. ........... A61B 18/1445 128/898 |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,077,853 B2 | 7/2006 | Kramer et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,179,271 B2 | 2/2007 | Friedman et al. |
| 7,186,253 B2 | 3/2007 | Truckai et al. |

(56) References Cited

U.S. PATENT DOCUMENTS

| | | | |
|---|---|---|---|
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 * | 6/2007 | Dumbauld ......... A61B 18/1445 606/45 |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,273,483 B2 | 9/2007 | Wiener et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,416,101 B2 | 8/2008 | Shelton, IV et al. |
| 7,422,139 B2 | 9/2008 | Shelton, IV et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,543,730 B1 | 6/2009 | Marczyk |
| 7,550,216 B2 | 6/2009 | Ofer et al. |
| 7,553,309 B2 | 6/2009 | Buysse et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,751 B2 | 5/2010 | Hughes et al. |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,726,537 B2 | 6/2010 | Olson et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,210 B2 | 8/2010 | Shelton, IV et al. |
| 7,766,910 B2 | 8/2010 | Hixson et al. |
| 7,770,775 B2 | 8/2010 | Shelton, IV et al. |
| 7,775,972 B2 | 8/2010 | Brock et al. |
| 7,776,037 B2 | 8/2010 | Odom |
| 7,780,651 B2 | 8/2010 | Madhani et al. |
| 7,780,663 B2 | 8/2010 | Yates et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,861,906 B2 | 1/2011 | Doll et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| 7,935,114 B2 | 5/2011 | Takashino et al. |
| 7,951,165 B2 | 5/2011 | Golden et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,038,693 B2 | 10/2011 | Allen |
| 8,056,720 B2 | 11/2011 | Hawkes |
| 8,058,771 B2 | 11/2011 | Giordano et al. |
| 8,061,014 B2 | 11/2011 | Smith et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,221,415 B2 | 7/2012 | Francischelli |
| 8,236,020 B2 | 8/2012 | Smith et al. |
| 8,241,235 B2 | 8/2012 | Kahler et al. |
| 8,241,284 B2 | 8/2012 | Dycus et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |

(56) References Cited

U.S. PATENT DOCUMENTS

| | | |
|---|---|---|
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,333,778 B2 | 12/2012 | Smith et al. |
| 8,333,779 B2 | 12/2012 | Smith et al. |
| 8,334,468 B2 | 12/2012 | Palmer et al. |
| 8,338,726 B2 | 12/2012 | Palmer et al. |
| 8,357,158 B2 | 1/2013 | McKenna et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,059 B2 | 2/2013 | Deville et al. |
| 8,377,085 B2 | 2/2013 | Smith et al. |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,430,876 B2 | 4/2013 | Kappus et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,496,682 B2 | 7/2013 | Guerra et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| D695,407 S | 12/2013 | Price et al. |
| 8,613,383 B2 | 12/2013 | Beckman et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,647,350 B2 | 2/2014 | Mohan et al. |
| 8,663,220 B2 | 3/2014 | Wiener et al. |
| 8,663,222 B2 | 3/2014 | Anderson et al. |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,028,494 B2 | 5/2015 | Shelton, IV et al. |
| 9,028,519 B2 | 5/2015 | Yates et al. |
| 9,044,243 B2 | 6/2015 | Johnson et al. |
| 9,044,256 B2 | 6/2015 | Cadeddu et al. |
| 9,055,961 B2 | 6/2015 | Manzo et al. |
| 9,060,770 B2 | 6/2015 | Shelton, IV et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,101,385 B2 | 8/2015 | Shelton, IV et al. |
| 9,119,657 B2 | 9/2015 | Shelton, IV et al. |
| 9,125,662 B2 | 9/2015 | Shelton, IV |
| 9,149,324 B2 | 10/2015 | Huang et al. |
| 9,149,325 B2 | 10/2015 | Worrell et al. |
| 9,168,085 B2 | 10/2015 | Juzkiw et al. |
| 9,179,912 B2 | 11/2015 | Yates et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,216,050 B2 | 12/2015 | Condie et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,259,265 B2 | 2/2016 | Harris et al. |
| 9,265,926 B2 | 2/2016 | Strobl et al. |
| 9,277,962 B2 | 3/2016 | Koss et al. |
| 9,283,027 B2 | 3/2016 | Monson et al. |
| 9,283,045 B2 | 3/2016 | Rhee et al. |
| 9,295,514 B2 | 3/2016 | Shelton, IV et al. |
| 9,314,292 B2 | 4/2016 | Trees et al. |
| 9,326,788 B2 | 5/2016 | Batross et al. |
| 9,333,025 B2 | 5/2016 | Monson et al. |
| 9,351,754 B2 | 5/2016 | Vakharia et al. |
| 9,375,232 B2 | 6/2016 | Hunt et al. |
| 9,375,267 B2 | 6/2016 | Kerr et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,510,906 B2 | 12/2016 | Boudreaux et al. |
| 9,522,029 B2 | 12/2016 | Yates et al. |
| 2002/0022836 A1 | 2/2002 | Goble et al. |
| 2002/0049551 A1 | 4/2002 | Friedman et al. |
| 2002/0107517 A1 | 8/2002 | Witt et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0216722 A1 | 11/2003 | Swanson |

(56) References Cited

U.S. PATENT DOCUMENTS

| | | |
|---|---|---|
| 2003/0229344 A1 | 12/2003 | Dycus et al. |
| 2004/0019350 A1 | 1/2004 | O'Brien et al. |
| 2004/0054364 A1 | 3/2004 | Aranyi et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193148 A1 | 9/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0103819 A1 | 5/2005 | Racenet et al. |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0256405 A1 | 11/2005 | Makin et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0058825 A1 | 3/2006 | Ogura et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0106317 A1 | 5/2007 | Shelton, IV et al. |
| 2007/0118115 A1 | 5/2007 | Artale et al. |
| 2007/0146113 A1 | 6/2007 | Truckai et al. |
| 2007/0173803 A1 | 7/2007 | Wham et al. |
| 2007/0173811 A1 | 7/2007 | Couture et al. |
| 2007/0173813 A1 | 7/2007 | Odom |
| 2007/0175949 A1 | 8/2007 | Shelton, IV et al. |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0208340 A1 | 9/2007 | Ganz et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2007/0265616 A1 | 11/2007 | Couture et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0214967 A1 | 9/2008 | Aranyi et al. |
| 2008/0221565 A1 | 9/2008 | Eder et al. |
| 2008/0255642 A1 | 10/2008 | Zarins et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2008/0300588 A1 | 12/2008 | Groth et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0082766 A1 | 3/2009 | Unger et al. |
| 2009/0099582 A1 | 4/2009 | Isaacs et al. |
| 2009/0112229 A1 | 4/2009 | Omori et al. |
| 2009/0125026 A1 | 5/2009 | Rioux et al. |
| 2009/0125027 A1 | 5/2009 | Fischer |
| 2009/0131929 A1 | 5/2009 | Shimizu |
| 2009/0138003 A1 | 5/2009 | Deville et al. |
| 2009/0138006 A1 | 5/2009 | Bales et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0254080 A1 | 10/2009 | Honda |
| 2009/0287205 A1 | 11/2009 | Ingle |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0077648 A1* | 3/2011 | Lee .................. A61B 18/1445 606/51 |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0118754 A1 | 5/2011 | Dachs, II et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2011/0301605 A1 | 12/2011 | Homer |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0116265 A1 | 5/2012 | Houser et al. |
| 2012/0116379 A1 | 5/2012 | Yates et al. |
| 2012/0116380 A1 | 5/2012 | Madan et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0138660 A1 | 6/2012 | Shelton, IV |
| 2012/0150170 A1 | 6/2012 | Buysse et al. |
| 2012/0150192 A1 | 6/2012 | Dachs, II et al. |
| 2012/0172859 A1 | 7/2012 | Condie et al. |

(56) References Cited

U.S. PATENT DOCUMENTS

| | | |
|---|---|---|
| 2012/0265196 A1 | 10/2012 | Turner et al. |
| 2012/0265241 A1 | 10/2012 | Hart et al. |
| 2012/0296371 A1 | 11/2012 | Kappus et al. |
| 2012/0323238 A1 | 12/2012 | Tyrrell et al. |
| 2013/0023925 A1 | 1/2013 | Mueller |
| 2013/0030428 A1 | 1/2013 | Worrell et al. |
| 2013/0030433 A1 | 1/2013 | Heard |
| 2013/0035685 A1 | 2/2013 | Fischer et al. |
| 2013/0079762 A1 | 3/2013 | Twomey et al. |
| 2013/0085496 A1 | 4/2013 | Unger et al. |
| 2013/0123776 A1 | 5/2013 | Monson et al. |
| 2013/0123782 A1* | 5/2013 | Trees ............... H02J 7/00 606/45 |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0253502 A1 | 9/2013 | Aronow et al. |
| 2013/0296843 A1 | 11/2013 | Boudreaux et al. |
| 2013/0338661 A1 | 12/2013 | Behnke, II |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0094801 A1 | 4/2014 | Boudreaux et al. |
| 2014/0194875 A1 | 4/2014 | Reschke et al. |
| 2014/0180281 A1 | 6/2014 | Rusin |
| 2014/0194874 A1 | 7/2014 | Dietz et al. |
| 2014/0194915 A1 | 7/2014 | Johnson et al. |
| 2014/0214019 A1 | 7/2014 | Baxter, III et al. |
| 2014/0228844 A1 | 8/2014 | Hörlle et al. |
| 2014/0257284 A1 | 9/2014 | Artale |
| 2014/0303551 A1 | 10/2014 | Germain et al. |
| 2014/0316408 A1 | 10/2014 | Davison et al. |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0133929 A1 | 5/2015 | Evans et al. |
| 2015/0141981 A1 | 5/2015 | Price et al. |
| 2015/0190189 A1 | 7/2015 | Yates et al. |
| 2015/0196352 A1 | 7/2015 | Beckman et al. |
| 2015/0230853 A1 | 8/2015 | Johnson et al. |
| 2015/0230861 A1 | 8/2015 | Woloszko et al. |
| 2015/0265347 A1 | 9/2015 | Yates et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2016/0045248 A1 | 2/2016 | Unger et al. |
| 2016/0051315 A1 | 2/2016 | Boudreaux |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0135875 A1 | 5/2016 | Strobl et al. |
| 2016/0157927 A1 | 6/2016 | Corbett et al. |
| 2016/0175024 A1 | 6/2016 | Yates et al. |
| 2016/0175028 A1 | 6/2016 | Trees et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |
| 2016/0199123 A1 | 7/2016 | Thomas et al. |
| 2016/0199125 A1 | 7/2016 | Jones |
| 2016/0228171 A1 | 8/2016 | Boudreaux |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296268 A1 | 10/2016 | Gee et al. |
| 2016/0296270 A1 | 10/2016 | Strobl et al. |
| 2016/0296271 A1 | 10/2016 | Danziger et al. |
| 2016/0302844 A1 | 10/2016 | Strobl et al. |

FOREIGN PATENT DOCUMENTS

| | | |
|---|---|---|
| DE | 4300307 A1 | 7/1994 |
| DE | 19608716 C1 | 4/1997 |
| DE | 29623113 U1 | 10/1997 |
| DE | 20004812 U1 | 9/2000 |
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0557806 B1 | 5/1998 |
| EP | 0640317 B1 | 9/1999 |
| EP | 0722696 B1 | 12/2002 |
| EP | 1293172 B1 | 4/2006 |
| EP | 0875209 B1 | 5/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1435852 B1 | 12/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1510178 B1 | 6/2011 |
| EP | 1728475 B1 | 8/2011 |
| EP | 2353518 A1 | 8/2011 |
| EP | 2529681 A1 | 12/2012 |
| EP | 1767164 B1 | 1/2013 |
| EP | 2316359 B1 | 3/2013 |
| EP | 2578172 A2 | 4/2013 |
| EP | 2508143 B1 | 2/2014 |
| GB | 2472216 A | 2/2011 |
| JP | H08-229050 A | 9/1996 |
| JP | 2008-018226 A | 1/2008 |
| JP | 5714508 B2 | 5/2015 |
| WO | WO 81/03272 A1 | 11/1981 |
| WO | WO 93/07817 A1 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |

(56) References Cited

FOREIGN PATENT DOCUMENTS

| | | |
|---|---|---|
| WO | WO 99/23960 A1 | 5/1999 |
| WO | WO 99/40857 A1 | 8/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/062241 A1 | 8/2002 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/078051 A2 | 9/2004 |
| WO | WO 2004/112618 A2 | 12/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2006/119139 A2 | 11/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/008672 A2 | 1/2011 |
| WO | WO 2011/084768 A1 | 7/2011 |
| WO | WO 2011/089717 A1 | 7/2011 |
| WO | WO 2011/144911 A1 | 11/2011 |
| WO | WO 2012/044606 A2 | 4/2012 |
| WO | WO 2012/166510 A1 | 12/2012 |
| WO | WO 2013/034629 A1 | 3/2013 |
| WO | WO 2013/062978 A2 | 5/2013 |
| WO | WO 2013/102602 A2 | 7/2013 |
| WO | WO 2013/154157 A1 | 10/2013 |
| WO | WO 2015/197395 A8 | 12/2015 |

OTHER PUBLICATIONS

Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomechanical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/d1-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, Engineering Formulas § Z.7 (7th ed. 1997).
National Semiconductors Temperature Sensor Handbook—http://www.national.com/appinfo/tempsensors/files/temphb.pdf; accessed online: Apr. 1, 2011.
Glaser and Subak-Sharpe, Integrated Circuit Engineering, Addison-Wesley Publishing, Reading, MA (1979). (book—not attached).
Wright, et al., "Time-Temperature Equivalence of Heat-Induced Changes in Cells and Proteins," Feb., 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Erbe Electrosurgery VIO0® 200 S, (2012), p. 7, 12 pages, accessed Mar. 31, 2014 at http://www.erbe-med.com/erbe/media/Marketingmaterialien/85140-170_ERBE_EN_VIO_200_S_D027541.
Jang, J. et al. "Neuro-fuzzy and Soft Computing." Prentice Hall, 1997, pp. 13-89, 199-293, 335-393, 453-496, 535-549.
Douglas, S.C. "Introduction to Adaptive Filter". Digital Signal Processing Handbook. Ed. Vijay K. Madisetti and Douglas B. Williams. Boca Raton: CRC Press LLC, 1999.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Leonard I. Malis, M.D., "The Value of Irrigation During Bipolar Coagulation," 1989.
U.S. Appl. No. 15/265,293, filed Sep. 14, 2016.
U.S. Appl. No. 15/258,570, filed Sep. 7, 2016.
U.S. Appl. No. 15/258,578, filed Sep. 7, 2016.

(56) References Cited

OTHER PUBLICATIONS

U.S. Appl. No. 15/258,586, filed Sep. 7, 2016.
U.S. Appl. No. 15/258,598, filed Sep. 7, 2016.
U.S. Appl. No. 12/576,529, filed Oct. 9, 2009.

* cited by examiner

| COMPONENT | MARKING | COLD CUT | MODE STANDARD | SEAL ONLY |
|---|---|---|---|---|
| KNIFE | KNIFE IS ENABLED AFTER JAW CLOSURE | ENABLED BY LEVER CLOSURE SWITCH | KNIFE IS ENABLED AFTER ENERGY | KNIFE IS PERMANENTLY LOCKED |
| ENERGY | NO ACTION REQUIRED. ENERGY ACTIVATES UPON JAW CLOSURE | ENERGY IS DISABLED | AFTER ENERGY ENABLE CUTTING | AFTER LEVER CLOSURE, ENABLE ENERGY |
| JAW CLOSURE | ONCE LEVER IS LOCKED IN THE JAW CLOSED STATE, ENERGY IS ACTIVATED AND THE KNIFE IS ENABLED | END OF LEVER SWITCH ENABLES KNIFE | ONCE THE JAWS ARE CLOSED ENERGY IS ENABLED | ONCE THE JAWS ARE CLOSED ENERGY IS ENABLED |

SELECT MODALITY ON HANDLE KNOB SELECTOR

| STEPS | | | | |
|---|---|---|---|---|
| 1 | CLOSE JAWS | CLOSE LEVER | CLOSE JAWS | CLOSE JAWS |
| 2 | ENERGY IS ACTIVATED UPON JAW CLOSURE | KNIFE IS UNLOCKED | APPLY ENERGY | ENABLE ENERGY |
| 3 | JAW CLOSURE | FIRE KNIFE | KNIFE IS UNLOCKED | |
| 4 | KNIFE IS UNLOCKED | | FIRE KNIFE | |
| 5 | FIRE KNIFE | | | |

FIG. 4B

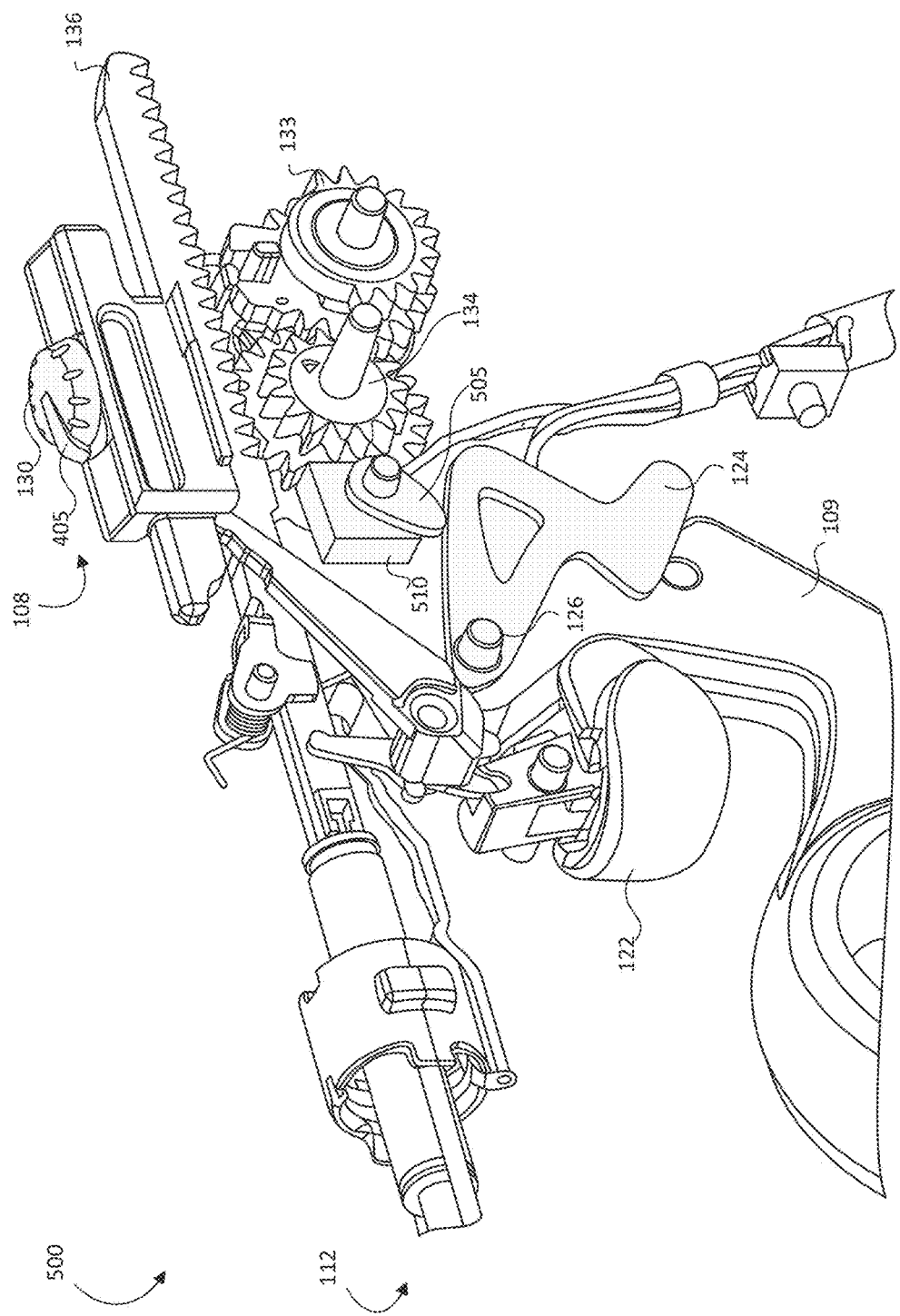

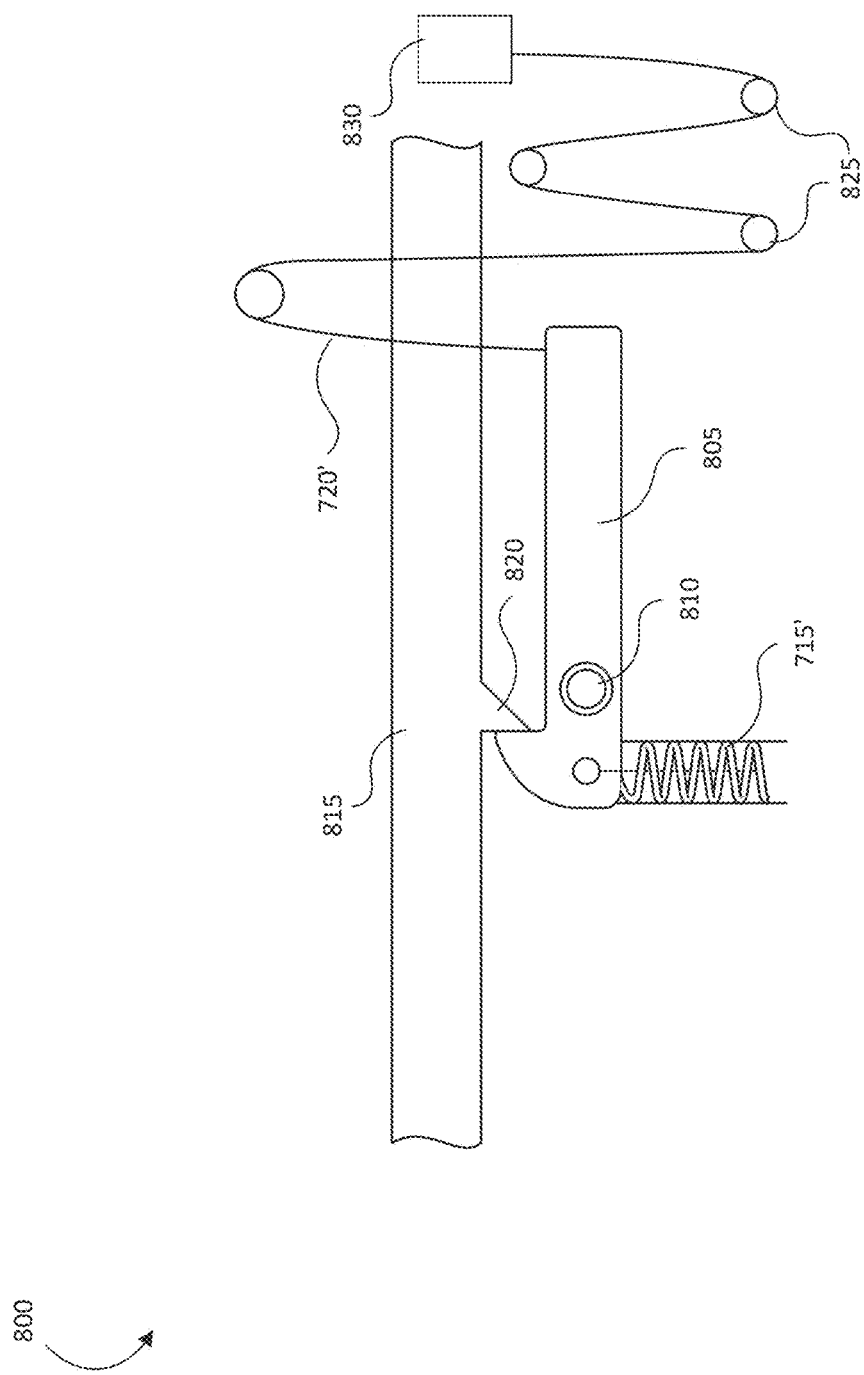

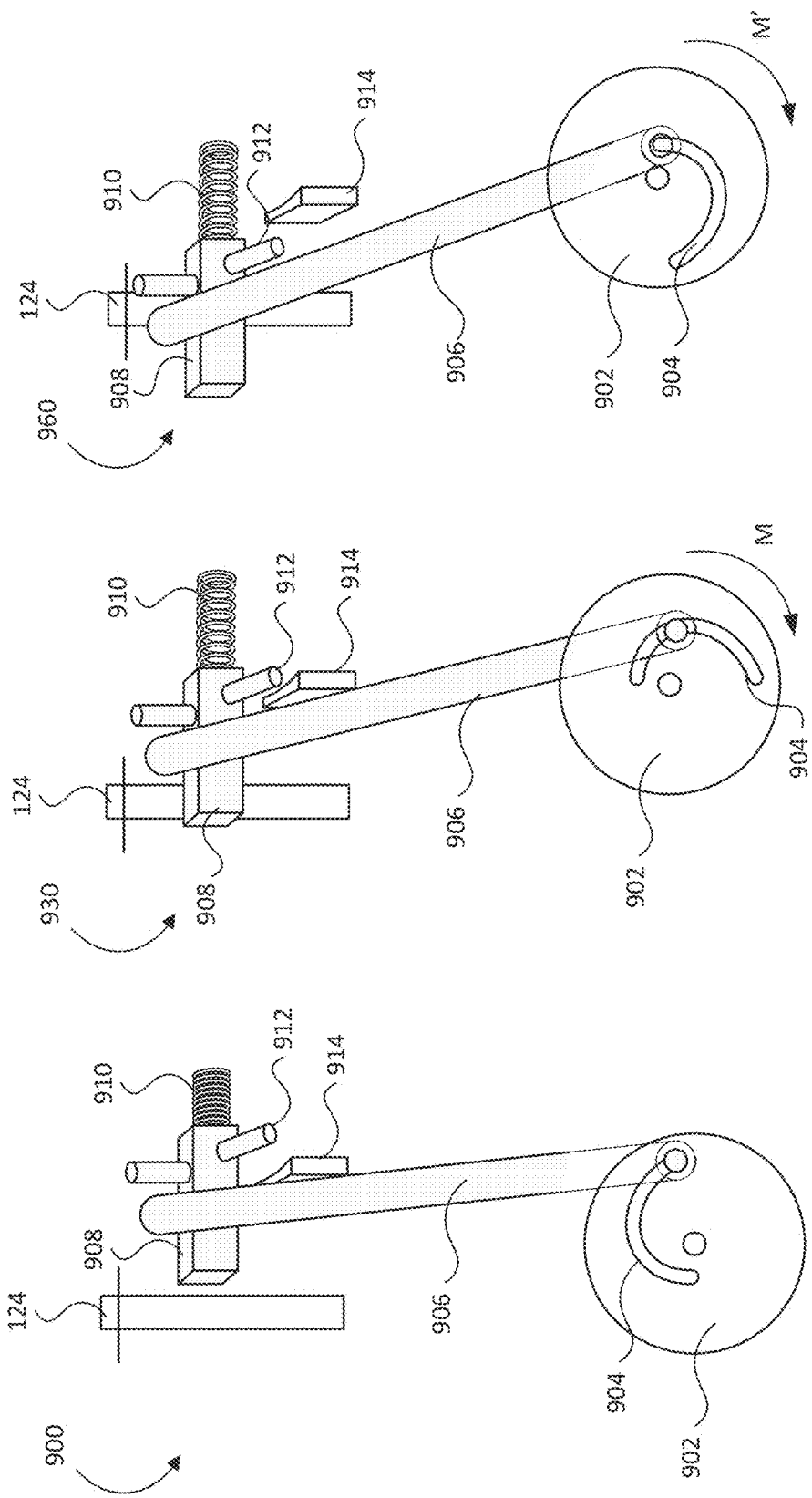

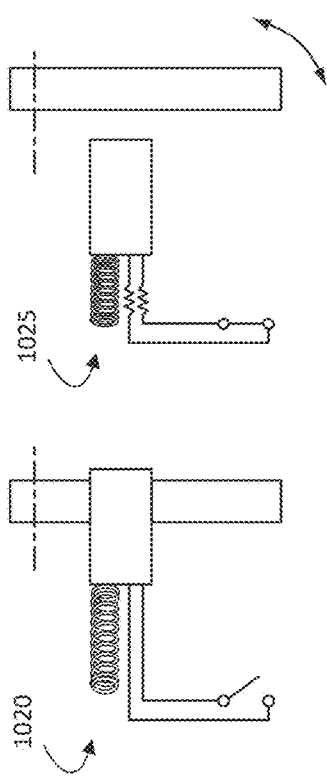
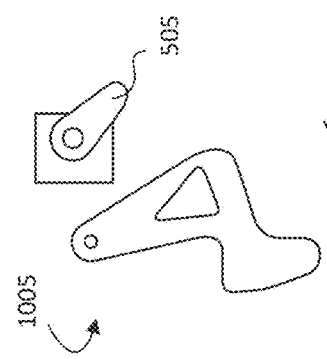
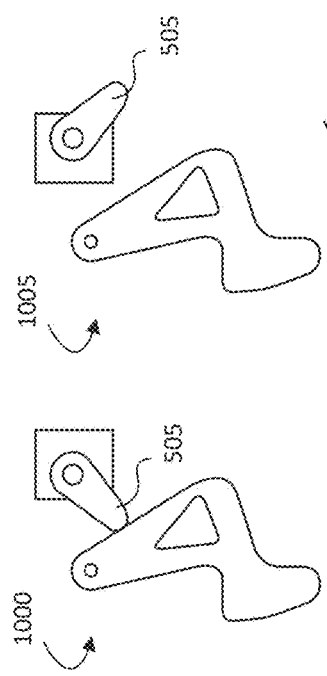
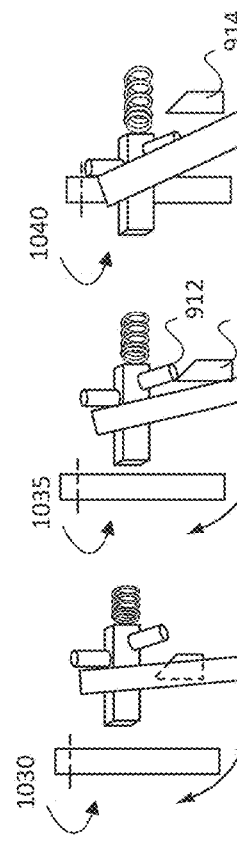
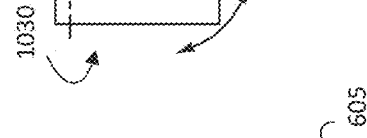
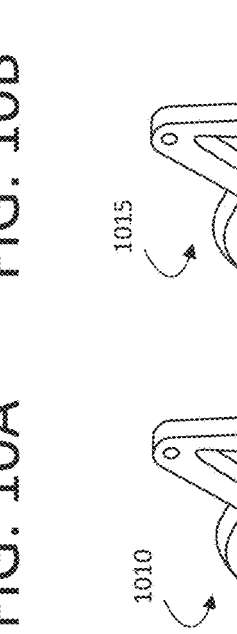
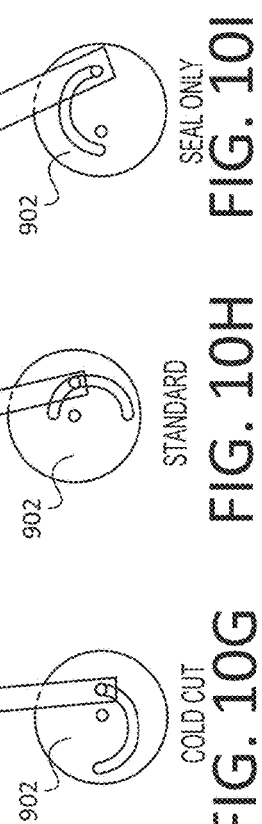
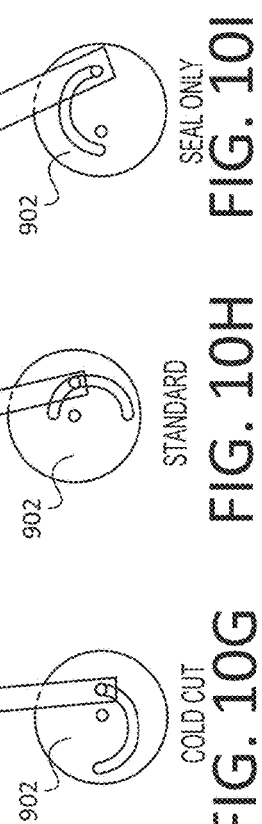
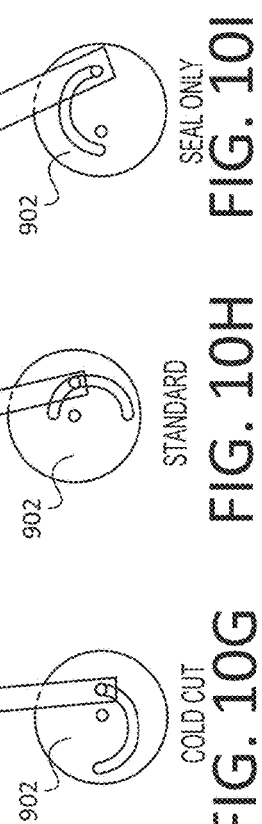

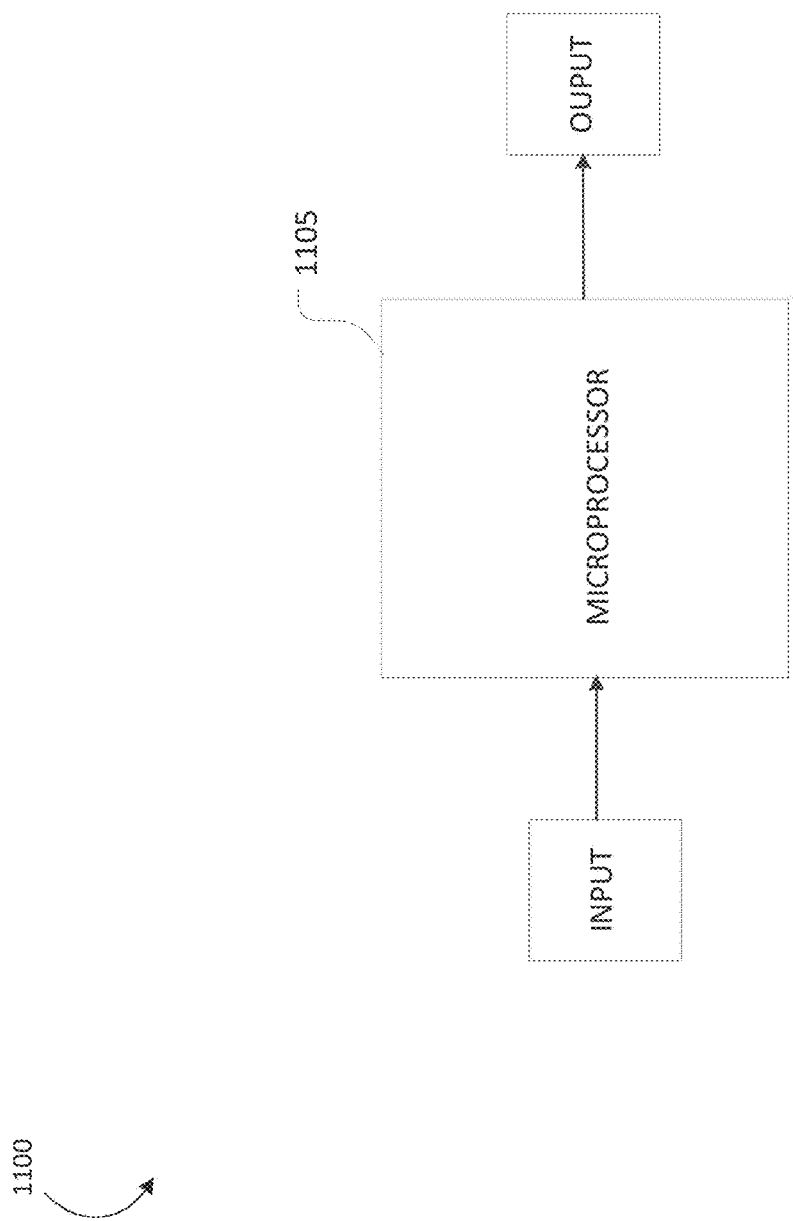

RF TISSUE SEALER WITH MODE SELECTION

INTRODUCTION

The present disclosure is related generally to electrosurgical devices with various mechanisms for clamping and treating tissue. In particular, the present disclosure is related to electrosurgical devices with a radio frequency (RF) tissue sealer with a mode selection assembly.

Conventional electrosurgical devices often lack functionality to address multiple surgical scenarios. For example, some surgical scenarios call for cutting tissue while quickly applying electrosurgical energy to seal the tissue. Other scenarios call for only cutting tissue without applying any electrosurgical energy. Yet other scenarios call for only applying energy without cutting tissue. For safety and ease of use, it is desirable to provide mechanisms to a surgical device to enable and disable functionality only when said functionality is intended to be used.

While several devices have been made and used, it is believed that no one prior to the inventors has made or used the device described in the appended claims.

SUMMARY

In some embodiments, a surgical instrument is provided.

1. In one example, the surgical instrument may include an end effector comprising a movable jaw; at least one electrode; and a cutting element slidably movable within the end effector; a handle assembly comprising: an energy button configured to deliver energy to the at least one electrode; a trigger plate operably coupled to a jaw closure mechanism, the trigger plate configured to close the movable jaw; a firing plate operably coupled to a cutting element drive mechanism, the firing plate configured to drive the cutting element independently of the jaw closure mechanism; a cutting element lockout mechanism coupled to the cutting element drive mechanism and configured to disable movement of the cutting element; and a mode selection assembly coupled to the energy button and the cutting element lockout mechanism, the mode selection assembly comprising a knob configured to rotate between a first mode and a second mode, wherein: in the first mode, the mode selection assembly is configured to enable the energy to be delivered to the at least one electrode after the movable jaw is closed; enable movement of the cutting element after the energy is applied by transitioning the cutting element lockout mechanism to the unlocked state; and enable the firing plate to drive the cutting element; and in the second mode, the mode selection assembly is configured to disable the energy from being delivered to the at least one electrode; enable movement of the cutting element after the movable jaw is closed by transitioning the cutting element lockout mechanism to the unlocked state; and enable the firing plate to drive the cutting element.

2. Another example includes the surgical instrument of example 1, wherein the mode selection assembly further comprises a third mode and the knob is configured to rotate between the first, second, and third modes, wherein: in the third mode, the mode selection assembly is further configured to enable the energy to be delivered to the at least one electrode after the movable jaw is closed; and disable movement of the cutting element by transitioning the cutting element lockout mechanism to the locked state.

3. Another example includes the surgical instrument of either example 1 or 2, wherein the mode selection assembly further comprises a fourth mode and the knob is configured to rotate between the first, second, and fourth modes, wherein: in the fourth mode, the mode selection assembly is further configured to automatically deliver the energy to the at least one electrode after the movable jaw is closed; enable movement of the cutting element after the energy is delivered by transitioning the cutting element lockout mechanism to the unlocked state; and enable the firing plate to drive the cutting element.

4. Another example includes the surgical instrument of any of examples 1-3, wherein the cutting element lockout mechanism comprises an electric motor coupled to the mode selection assembly; and a mechanical switch coupled to the electric motor and configured to rotate between the locked state and the unlocked state; wherein: a first electric signal applied to the electric motor causes the mechanical switch to rotate to the locked state and prevent complete movement of the trigger plate; and a second electric signal applied to the electric motor causes the mechanical switch to rotate to the unlocked state and allow complete movement of the trigger plate.

5. Another example includes the surgical instrument of any of examples 1-3, wherein the cutting element lockout mechanism comprises a solenoid coupled to the mode selection assembly; and a pin coupled to the solenoid and configured to transition between the locked state and the unlocked state; wherein: a first electric signal applied to the solenoid causes the pin to protrude outside the solenoid in the locked state and prevent complete movement of the trigger plate; and a second electric signal applied to the solenoid causes the pin to retract inside the solenoid in the unlocked state and allow complete movement of the trigger plate.

6. Another example includes the surgical instrument of any of examples 1-3, wherein the cutting element lockout mechanism comprises a control circuit electrically coupled to the mode selection assembly; a wire comprising shape memory and elasticity characteristics and coupled to the control circuit, the wire configured to change shape by a current is applied to it by the control circuit due to the shape memory and elasticity characteristics; a lockout block coupled to the wire; and a spring coupled to the lockout block positioned parallel to the wire.

7. Another example includes the surgical instrument of example 6, wherein: an electric signal applied to the control circuit causes the wire to contract and pull the lockout block away from the trigger plate to allow for complete movement of the trigger plate; and the electric signal not applied to the control circuit causes the wire to relax and the spring to push the lockout block toward the trigger plate to prevent complete movement of the trigger plate.

8. Another example includes the surgical instrument of any of examples 1-3, wherein the cutting element lockout mechanism comprises a dial coupled to the mode selection assembly and configured to rotate coaxially with the knob, the dial comprising a curved groove; a beam comprising a proximal end coupled to a hinge in the curved groove and configured to slide within the curved groove upon rotation of the dial; a lockout block coupled to the beam; and a spring coupled to the lockout block.

9. Another example includes the surgical instrument of example 8, wherein: a first rotation in a first direction applied to the dial causes the lockout block to protrude beyond the trigger plate in the locked state and prevent complete movement of the trigger plate; and a second rotation in a second direction applied to the dial causes the lockout block to retract away from the trigger plate in the unlocked state and allow complete movement of the trigger plate.

10. In another example, a surgical instrument comprises: an end effector comprising a movable jaw; at least one electrode; and a cutting element slidably movable within the end effector; a handle assembly comprising: an energy button configured to deliver energy to the at least one electrode located in the end effector; a trigger plate operably coupled to a jaw closure mechanism, the trigger plate configured to close the movable jaw; a firing plate operably coupled to a cutting element drive mechanism, the firing plate configured to drive the cutting element independently of the jaw closure mechanism; a cutting element lockout mechanism coupled to the cutting element drive mechanism, wherein the cutting element is configured to move between a locked state and an unlocked state to: disable movement of the cutting element in a locked state; and enable movement of the cutting element in an unlocked state; and a mode selection assembly coupled to the energy button and the cutting element lockout mechanism, the mode selection assembly comprising a knob configured to rotate between a first mode, a second mode, a third mode, and a fourth mode, wherein: in the first mode, the mode selection assembly is configured to enable the energy to be delivered to the at least one electrode after the movable jaw is closed; enable movement of the cutting element after the energy is applied by transitioning the cutting element lockout mechanism to the unlocked state; and enable the firing plate to drive the cutting element; in the second mode, the mode selection assembly is configured to disable the energy from being delivered to the at least one electrode; enable movement of the cutting element after the movable jaw is closed by transitioning the cutting element lockout mechanism to the unlocked state; and enable the firing plate to drive the cutting element; in the third mode, the mode selection assembly is configured to enable the energy to be delivered to the at least one electrode after the movable jaw is closed; and disable movement of the cutting element by transitioning the cutting element lockout mechanism to the locked state; and in the fourth mode, the mode selection assembly is configured to automatically deliver the energy to the at least one electrode after the movable jaw is closed; enable movement of the cutting element after the energy is delivered by transitioning the cutting element lockout mechanism to the unlocked state; and enable the firing plate to drive the cutting element.

11. Another example includes the surgical instrument of example 10, wherein the cutting element lockout mechanism comprises an electric motor coupled to the mode selection assembly; and a mechanical switch coupled to the electric motor and configured to rotate between the locked state and the unlocked state; wherein: a first electric signal applied to the electric motor causes the mechanical switch to rotate to the locked state and prevent complete movement of the trigger plate; and a second electric signal applied to the electric motor causes the mechanical switch to rotate to the unlocked state and allow complete movement of the trigger plate.

12. Another example includes the surgical instrument of example 10, wherein the cutting element lockout mechanism comprises a solenoid coupled to the mode selection assembly; and a pin coupled to the solenoid and configured to transition between the locked state and the unlocked state; wherein: a first electric signal applied to the solenoid causes the pin to protrude outside the solenoid in the locked state and prevent complete movement of the trigger plate; and a second electric signal applied to the solenoid causes the pin to retract inside the solenoid in the unlocked state and allow complete movement of the trigger plate.

13. Another example includes the surgical instrument of example 10, wherein the cutting element lockout mechanism comprises: a control circuit electrically coupled to the mode selection assembly; a wire comprising shape memory and elasticity characteristics and coupled to the control circuit, the wire configured to change shape by a current is applied to it by the control circuit due to the shape memory and elasticity characteristics; a lockout block coupled to the wire; and a spring coupled to the lockout block positioned parallel to the wire.

14. Another example includes the surgical instrument of example 13, wherein: an electric signal applied to the control circuit causes the wire to contract and pull the lockout block away from the trigger plate to allow for complete movement of the trigger plate; and the electric signal not applied to the control circuit causes the wire to relax and the spring to push the lockout block toward the trigger plate to prevent complete movement of the trigger plate.

15. Another example includes the surgical instrument of example 10, wherein the cutting element lockout mechanism comprises a dial coupled to the mode selection assembly and configured to rotate coaxially with the knob, the dial comprising a curved groove; a beam comprising a proximal end coupled to a hinge in the curved groove and configured to slide within the curved groove upon rotation of the dial; a lockout block coupled to the beam; and a spring coupled to the lockout block.

16. Another example includes the surgical instrument of example 15, wherein: a first rotation in a first direction applied to the dial causes the lockout block to protrude beyond the trigger plate in the locked state and prevent complete movement of the trigger plate; and a second rotation in a second direction applied to the dial causes the lockout block to retract away from the trigger plate in the unlocked state and allow complete movement of the trigger plate.

17. In another example, a surgical instrument comprises: an end effector comprising a movable jaw; at least one electrode; and a cutting element slidably movable within the end effector; a handle assembly comprising an energy button configured to deliver energy to the at least one electrode; a trigger plate operably coupled to a jaw closure mechanism, the trigger plate configured to close the movable jaw; a firing plate operably coupled to a cutting element drive mechanism, the firing plate configured to drive the cutting element independently of the jaw closure mechanism; a lockout mechanism coupled to the cutting element drive mechanism and, in a locked state, is configured to disable movement of the cutting element; and a mode selection assembly coupled to the energy button and the cutting element lockout mechanism, the mode selection assembly configured to select between different modes.

18. Another example includes the surgical instrument of example 17, wherein: in one mode, energy is enabled to be delivered to the at least one electrode after the movable jaw is closed; and in another mode, energy is disabled from being delivered to the at least one electrode.

19. Another example includes the surgical instrument of example 17, wherein: in one first mode, the cutting element is enabled to move after the energy is applied by transitioning the cutting element lockout mechanism to the unlocked state; and in another second mode, the cutting element is disabled from moving after the movable jaw is closed by transitioning the cutting element lockout mechanism to the unlocked state.

20. Another example includes the surgical instrument of any of examples 17-19, wherein in any mode, the firing plate is enabled to drive the cutting element only after energy is delivered to the at least one electrode and after the movable jaw is closed.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the embodiments described herein are set forth with particularity in the appended claims. The embodiments, however, both as to organization and methods of operation may be better understood by reference to the following description, taken in conjunction with the accompanying drawings as follows.

FIG. 4B shows a chart with the states of various components of the surgical instrument when the mode selection assembly is set to a particular mode, according to some embodiments.

FIG. 5A shows various mechanical and electrical components within the surgical instrument, comprising a mechanical system with an electric motor for locking and unlocking use of a cutting element of the surgical instrument, according to some embodiments.

FIG. 8A shows another example variation of the spring circuit system described in FIGS. 7A and 7B, this time including a hinge and a system of pulleys, according to some embodiments.

FIG. 9A shows another example of a locking system comprised of only mechanical components, according to some embodiments.

FIG. 9B shows a partial movement of the mechanical lockout mechanism for locking the trigger plate, according to some embodiments.

FIG. 9C shows the mechanical lockout mechanism in its fully locked state, according to some embodiments.

FIGS. 10A-10I provide a summary of the locked and unlocked states of various example implementations of the lockout mechanism for the cutting element, according to some embodiments.

FIG. 11A provides an example block diagram for performing electrical processes described in the present disclosures herein, according to some embodiments.

Figure 11B:
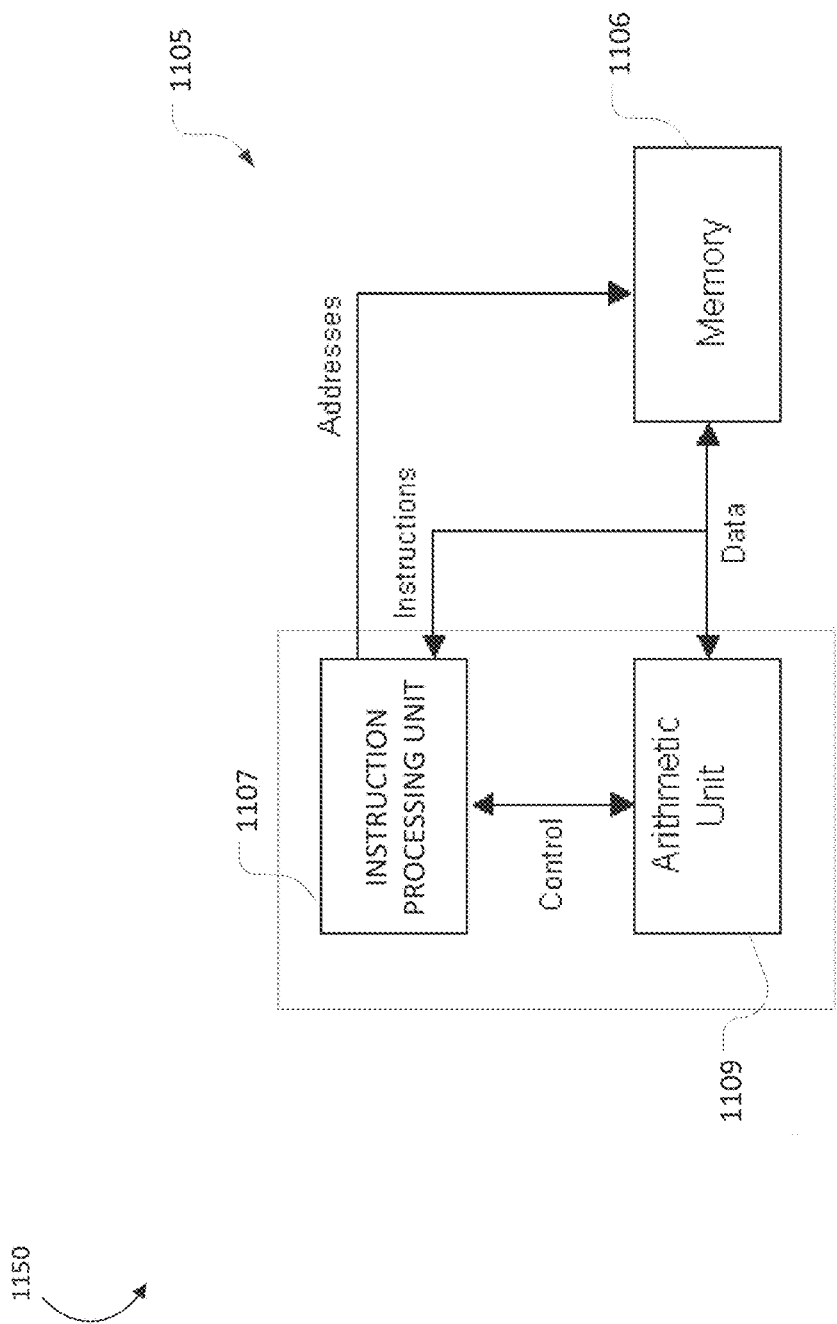

FIG. 11B provides a block diagram of the various elements of the microprocessor 1005, according to some embodiments.

DESCRIPTION

In the following detailed description, reference is made to the accompanying drawings, which form a part hereof. In the drawings, similar symbols and reference characters typically identify similar components throughout the several views, unless context dictates otherwise. The illustrative embodiments described in the detailed description, drawings, and claims are not meant to be limiting. Other embodiments may be utilized, and other changes may be made, without departing from the scope of the subject matter presented here.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings. Throughout this disclosure, the term "proximal" is used to describe the side of a component, e.g., a shaft, a handle assembly, etc., closer to a user operating the surgical instrument, e.g., a surgeon, and the term "distal" is used to describe the side of the component further from the user operating the surgical instrument.

Aspects of the present disclosure are presented for a surgical instrument for cutting and sealing tissue with a mode selection assembly. The mode selection assembly allows for the user to safely activate or disable a cutting functionality and a sealing functionality through use of electrosurgical energy. In some embodiments, the mode selection assembly allows for a more automated application of the electrosurgical energy and the cutting functionality when applied to a surgical site. In some embodiments, the mode selection assembly includes a knob that is configured to switch between the aforementioned settings. Various control mechanisms are also disclosed to lock and unlock the cutting element, such as a motorized locking mechanism, a solenoid locking mechanism, a mechanical mechanism and use of a nitinol wire. The inclusion of the mode selection assembly allows for a user to more safely utilize the surgical instrument by intentionally disabling functionality that may otherwise be inadvertently activated.

Figure 1:
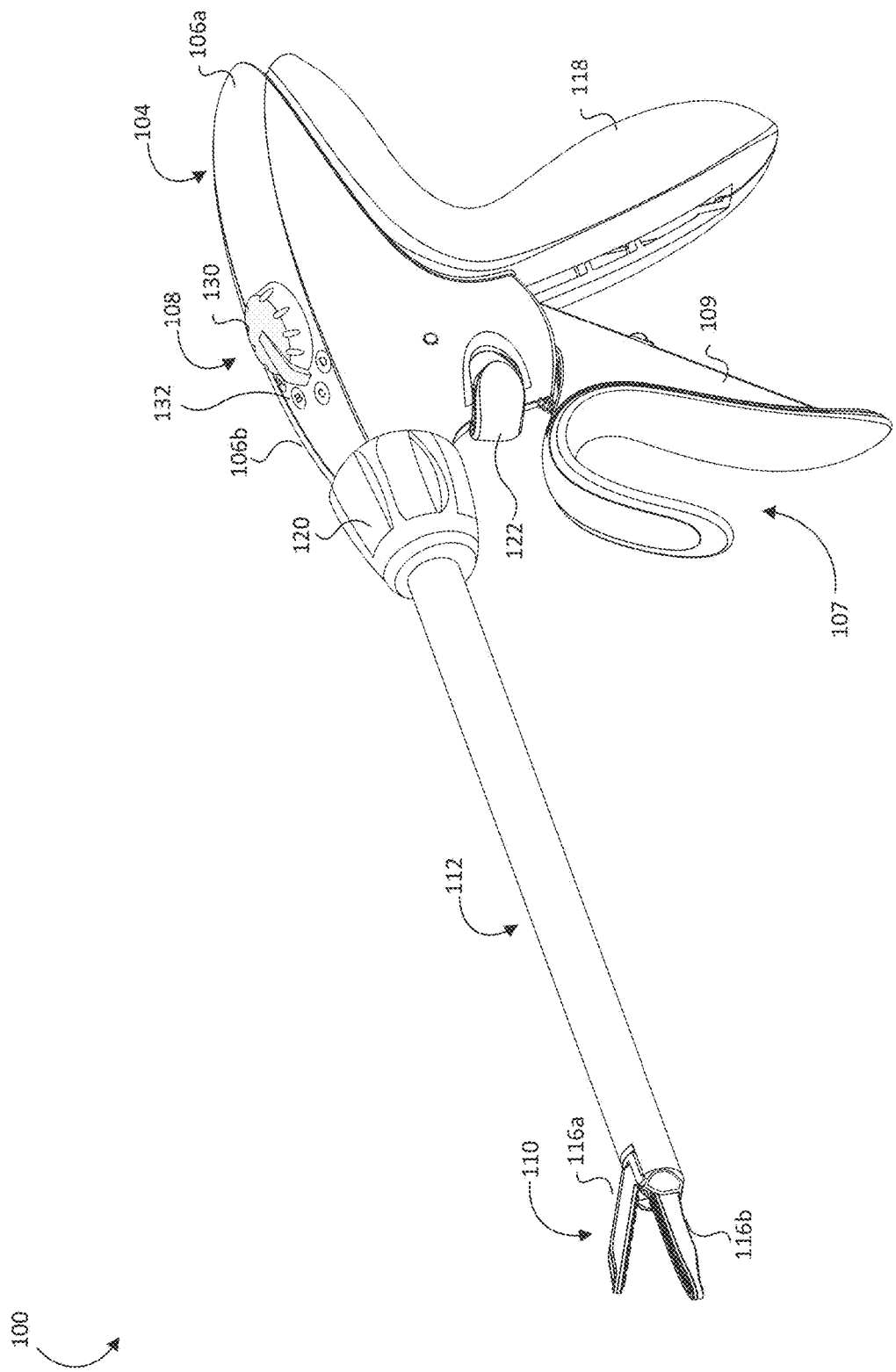
FIG. 1 illustrates a surgical instrument comprising sealing tissue mode selection assembly, according to some embodiments.

Turning now to the figures, FIG. 1 illustrates a surgical instrument 100 comprising a trigger assembly 107 and a closure system arrangement for closing the jaws 110 comprising a spring driven cam closure mechanism, according to some embodiments. The spring driven cam closure system is configured to close a set of opposing jaws 116a, 116b, and fire a cutting element in the end effector 110. The trigger assembly 107 is configured to clamp and fire an end effector 110 coupled to the shaft assembly 112 of the surgical instrument 100. In the example instrument shown in FIG. 1, the surgical instrument 100 includes a trigger assembly 107 and a tissue sealer mode selection assembly 108. In this view, a first jaw member 116a of an end effector 110 is fully open and the tissue sealer mode selection assembly 108 is turned to a first position. The tissue sealer mode selection assembly 108 includes a knob 130 that can be turned to four different settings, in this example. Various example settings include a "marching" setting, a "cold cut" setting, a "standard" setting, and a "seal only" setting. The tissue sealer mode selection assembly 108 is configured to allow operation of the surgical instrument 100 in multiple settings, such as allowing or preventing the cutting element to fire, and allowing or preventing electrosurgical energy to be applied to the end effector 110. The surgical instrument 100 also includes a handle assembly 104, a shaft assembly 112, and the end effector 110. The shaft assembly 112 comprises a proximal end and a distal end. The proximal end of the shaft assembly 112 is coupled to the distal end of the handle assembly 104. The end effector 110 is coupled to the distal end of the shaft assembly 112. The handle assembly 104 comprises a pistol grip 118. The handle assembly 104 comprises a left handle housing shroud 106a and a right handle housing shroud 106b. The trigger assembly 107 comprises a trigger 109 actuatable towards the pistol grip 118. The tissue sealer mode selection assembly 108 comprises a knob that is actuatable for adjusting or controlling the activation of the cutting element, the application of electrosurgical energy, and in some cases whether the surgical instrument 100 is to be operated manually or automatically. A rotatable shaft knob 120 is configured to rotate the shaft assembly 112 with respect to the handle assembly 104. The handle assembly 104 further comprises an energy button 122 configured to provide electrosurgical energy to one or more electrodes in the end effector 110.

The shaft assembly 112 comprises a closure/jaw actuator, a firing/cutting member actuator, and an outer sheath. In some embodiments, the outer sheath comprises the closure actuator. The outer sheath comprises one or more contact electrodes on a distal end configured to interface with the end effector 110. The one or more contact electrodes are operatively coupled to the energy button 122, the tissue sealer mode selection assembly 108, and an energy source (not shown).

The energy source may be suitable for therapeutic tissue treatment, tissue cauterization/sealing, as well as sub-therapeutic treatment and measurement. The energy button 122 controls the delivery of energy to the electrodes. As used throughout this disclosure, a button refers to a switch mechanism for controlling some aspect of a machine or a process. The buttons may be made out of a hard material such as usually plastic or metal. The surface may be formed or shaped to accommodate the human finger or hand, so as to be easily depressed or pushed. Buttons can be most often biased switches, even though many un-biased buttons (due to their physical nature) require a spring to return to their un-pushed state. Terms for the "pushing" of the button, may include press, depress, mash, and punch.

In some embodiments, the end effector 110 is coupled to the distal end of the shaft assembly 112. The end effector 110 comprises a first jaw member 116a and a second jaw member 116b. The first jaw member 116a is pivotally coupled to the second jaw member 116b. The first jaw member 116a is pivotally moveable with respect to the second jaw member 116b to grasp tissue therebetween. In some embodiments, the second jaw member 116b is fixed. In other embodiments, the first jaw member 116a and the second jaw member 116b are pivotally movable. The end effector 110 comprises at least one electrode. The electrode is configured to deliver electrosurgical energy. Energy delivered by the electrode may comprise, for example, radiofrequency (RF) energy, sub-therapeutic RF energy, ultrasonic energy, and/or other suitable forms of energy. In some embodiments, a cutting member (not shown) is receivable within a longitudinal slot defined by the first jaw member 116a and/or the second jaw member 116b. The cutting member is configured to cut tissue grasped between the first jaw member 116a and the second jaw member 116b. In some embodiments, the cutting member comprises an electrode for delivering energy, such as, for example, RF and/or ultrasonic energy.

In some embodiments, the tissue sealer mode selection assembly 108 may include a setting for a cutting element lockout mechanism. The cutting element lockout mechanism may be associated with a closure mechanism of the surgical instrument 100. In some settings, the cutting element lockout mechanism is configured to permits the cutting element, such as a knife, to fire in the end effector 110 when the jaw members 116a and 116b are a closed configuration and the cutting element is activated, such as through use of the trigger assembly 107. In other settings, the cutting element lockout mechanism is configured to disable use of the cutting element even when the jaw members 116a and 116b are in the closed configuration.

In some embodiments, the tissue sealer mode selection assembly 108 may include a setting for an energy lockout mechanism. The energy lockout mechanism can be associated with a closure mechanism of the surgical instrument 100. In certain instances, the energy lockout mechanism can be configured to permit energy delivery to the end effector 110 when the energy delivery button 122 is actuated if the jaw members 116a and 116b are in an open configuration. In certain instances, the energy lockout mechanism may be configured to deny energy delivery to the end effector 110 when the energy delivery button 122 is actuated if the jaw members 116a and 116b are in a closed configuration. In certain instances, the energy lockout mechanism automatically transitions from permitting the energy delivery to denying the energy delivery when the jaw members 116a and 116b are transitioned from the closed configuration to the open configuration, for example. In certain instances, the energy lockout mechanism automatically transitions from denying the energy delivery to permitting the energy delivery when the jaw members 116a and 116b are transitioned from the open configuration to the closed configuration, for example.

Depending on the setting, the tissue sealer mode selection assembly 108 may allow or deny the use of the cutting element through the cutting element lockout mechanism, in combination with allowing or denying the use of the energy through the use of the energy lockout mechanism. Example settings consistent with this description will be discussed more, below.

Figure 2:
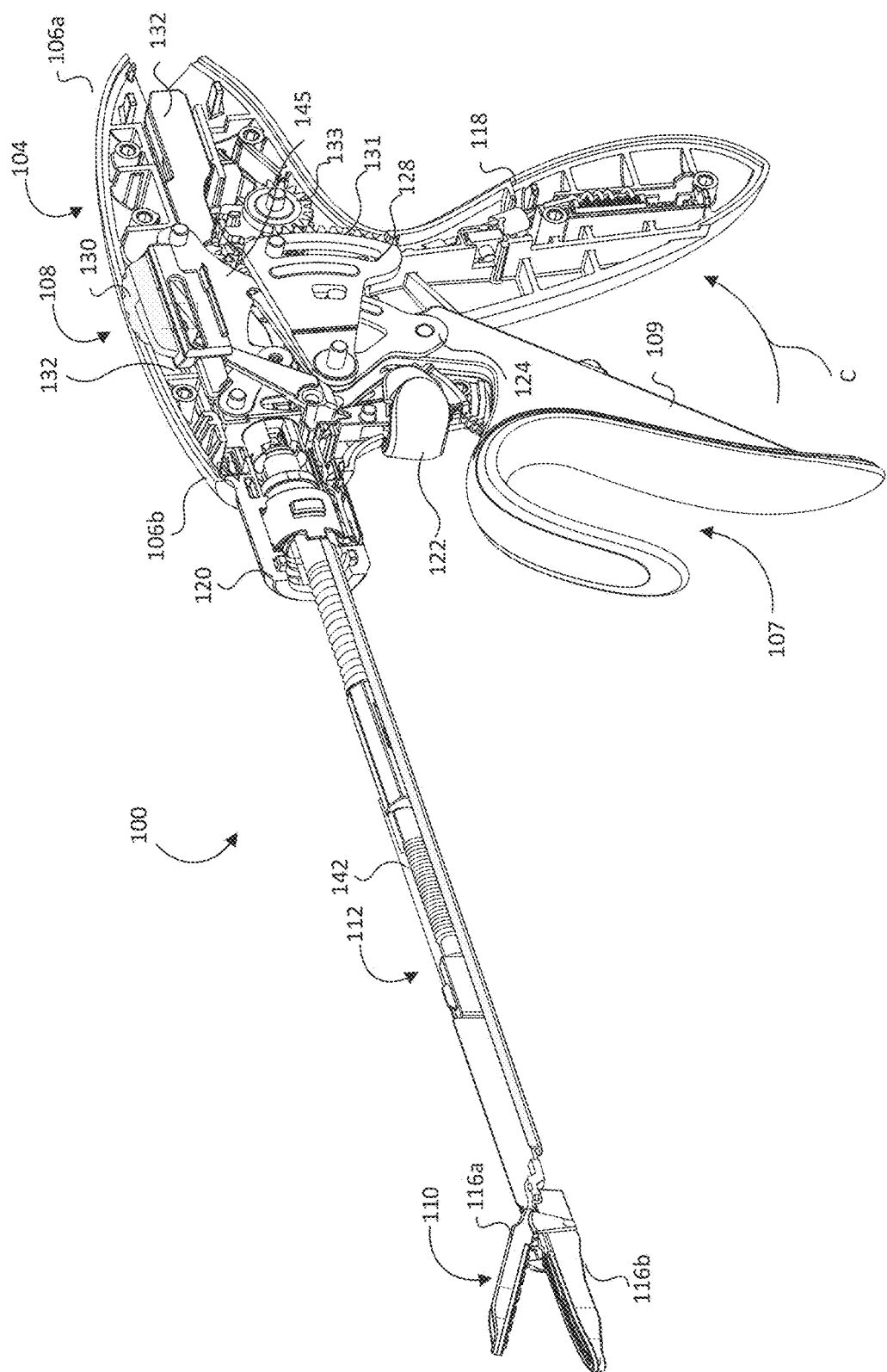
FIG. 2 is a perspective view of a handle assembly of the surgical instrument illustrated in FIG. 1 with the left handle housing shroud and several sheaths in the shaft assembly removed, according to some embodiments.

FIG. 2 is a perspective view of a handle assembly 104 of a surgical instrument 100 illustrated in FIG. 1, according to some embodiments, with the right housing shroud 106a and the outer and inner sheaths of the shaft assembly 112 removed to show some of the internal mechanisms. The left handle housing shroud 106b of the handle assembly 104 comprises the tissue sealer mode selection assembly 108. The knob 130 is located in a first position within the right handle housing shroud 106a. When tissue sealer mode selection assembly 108 is in a state that denies use of the electrode surgical energy, the energy button 122 may appear to be depressed to provide a visual indication to the clinician that tissue sealer mode selection assembly 108 has been disabled but without energizing the electrodes in the end effector 110 (FIG. 1). Similarly, when the tissue sealer mode selection assembly 108 is in a state that denies use of the cutting element, then manipulation of the trigger assembly 107 may not cause any knife to fire. In other cases, manipulation of the trigger assembly 107 may be hampered (e.g., the trigger may be pulled only halfway) when the tissue sealer mode selection assembly 108 is in the state that denies use of the cutting element.

The trigger assembly 107 comprises the necessary components for closing the jaw members 116a, 116b and firing the cutting member or knife bands 142. For example, in some embodiments, the trigger assembly 107 comprises a trigger plate 124 and firing plate 128 operatively coupled to the trigger 109. Squeezing the trigger 109 in direction C towards the pistol grip 118 rotates the trigger plate 124 which operates the toggle clamp 145 to advance a yoke 132 and a closure actuator distally to close the jaw members 116a, 116b of the end effector. Initial rotation of the trigger plate 124 also slightly rotates the firing plate 128. The firing plate 128 comprises a sector gear with a plurality of teeth 131 that engage and rotate a first pinion gear 133, which engages a second pinion gear 134 (see e.g., FIG. 5A) to advance a rack 136 (see e.g., FIG. 5A).

In some embodiments, the single trigger 109 fires the knife in the last set of degrees of the stroke, such as in the last ~29 degrees of stroke, in some embodiments. Rotation of the trigger plate 124 beyond a predetermined rotation such as, for example, the first rotation, causes rotation of the firing plate 128. Rotation of the firing plate 128 deploys a cutting member within the end effector 110. For example, in the illustrated embodiment, the firing plate 128 comprises a sector gear operably coupled to a rack 136 (FIG. 5A) through the first and second pinions 133, 134 (FIG. 5A). The firing plate 128 comprises a plurality of teeth 131 configured to interface with the first pinion 133. Rotation of the firing plate 128 rotates the first and second pinions 133, 134 (FIG. 5A), to drive the rack 136 (FIG. 5A) distally. Distal movement of the rack 136 (FIG. 5A) drives the cutting member actuator distally, causing deployment of the cutting member (e.g., knife) within the end effector 110.

Figure 3:
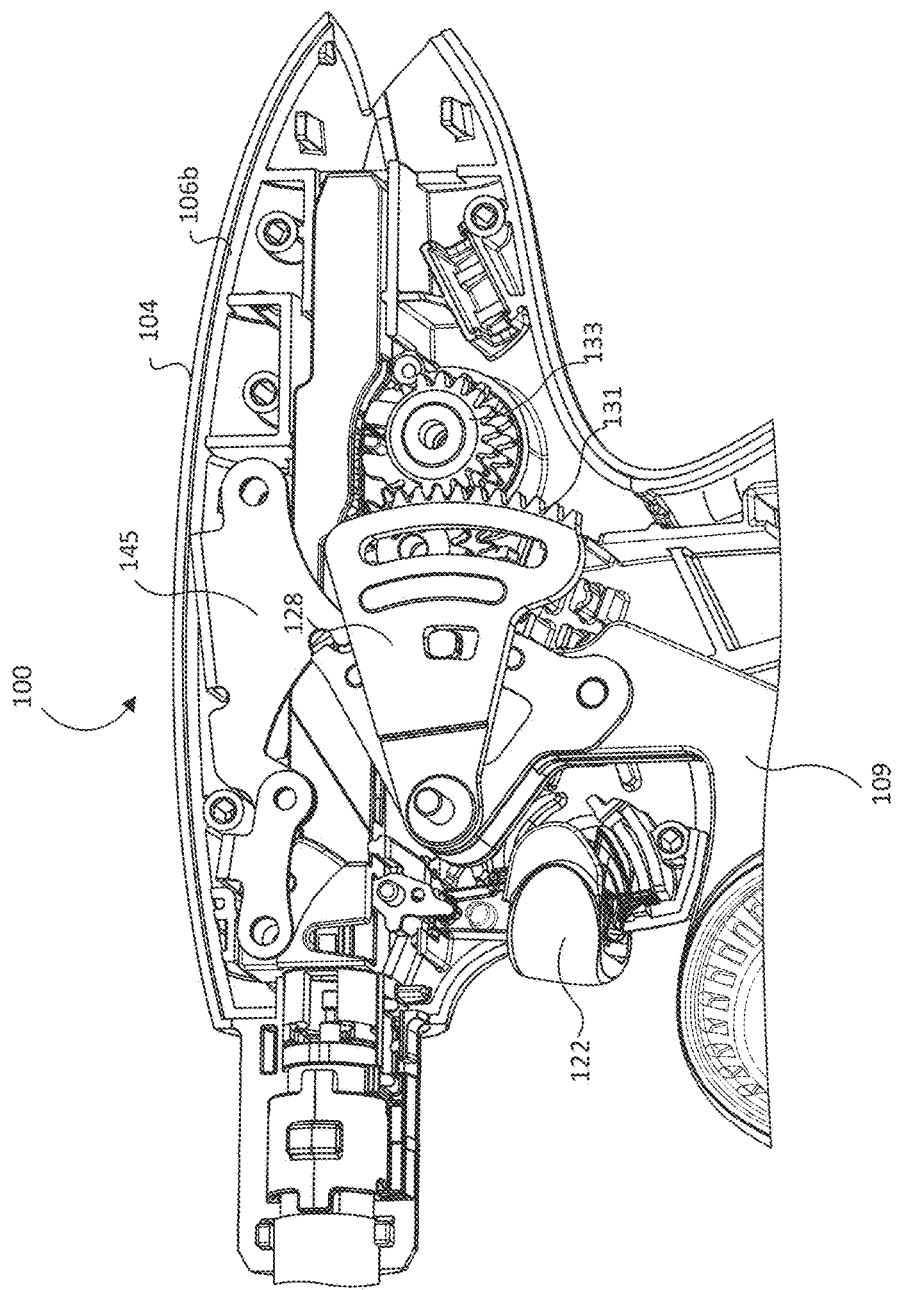
FIG. 3 is a side elevation view of a handle assembly of a surgical instrument, similar to the surgical instrument shown in FIGS. 1 and 2, with the left handle housing shroud removed, according to some embodiments.

FIG. 3 is a side elevation view of a handle assembly 104 of a surgical instrument 100, with the left handle housing shroud 106a removed to expose various mechanisms located within the handle assembly 104 and without the tissue sealer mode selection assembly 108 shown, according to some embodiments. The surgical instrument 100 shown in FIG. 3 operates in a manner similar to the surgical instrument described in connection with FIGS. 1 and 2.

Figure 4A:
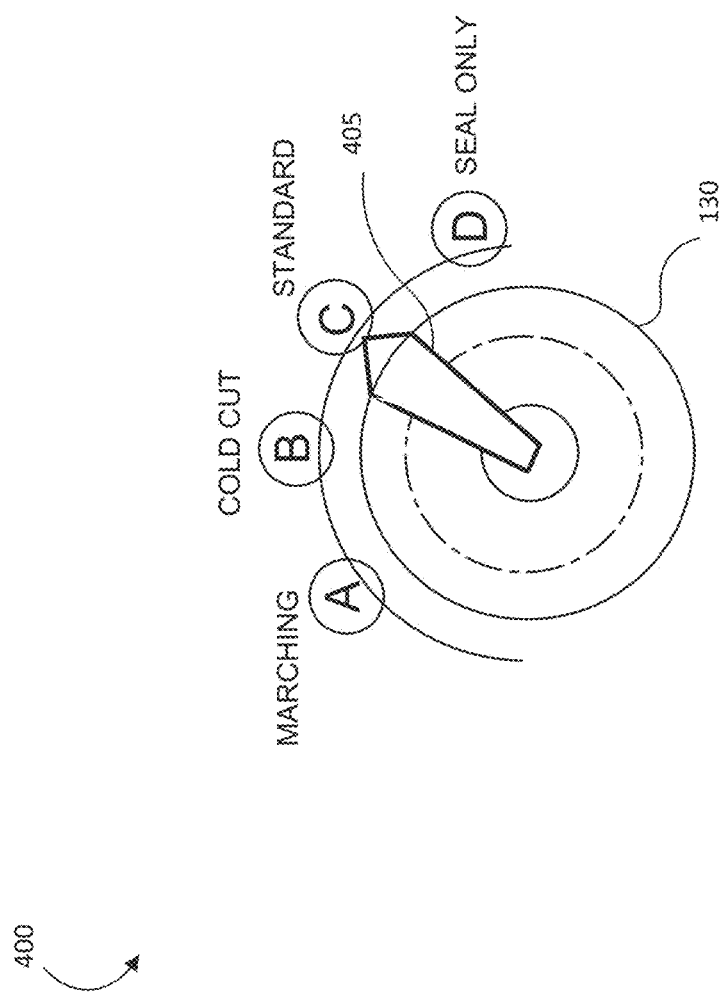
FIG. 4A shows example modes of the tissue sealer mode selection assembly, according to some embodiments.

Referring to FIG. 4A, illustration 400 shows example modes of the tissue sealer mode selection assembly 108, according to some embodiments. Shown here is a drawing of the knob 130 that can be twisted to select various modes for operating the surgical instrument 100. The knob 130 may include an arrow or pointer 405 to indicate which mode is selected. In this example, the mode selection assembly 108 includes four modes: a "marching" mode (A), a "cold cut" mode (B), a "standard" mode (C), and a "seal only" mode (D). In some embodiments, these modes may be linked to specific tones or messages on the assembly 108 that alert the user to which state they are operating the surgical instrument 100 in. When the knob 130 is rotated such that the arrow 405 points to a particular mode, then certain functionality of the surgical instrument 100 is disabled or enabled in accordance with the selected mode.

Referring to FIG. 4B, chart 450 shows the states of various components of the surgical instrument 100 when the mode selection assembly 108 is set to a particular mode, according to some embodiments. For example, column 455 includes three components that are varied depending on mode selected by the mode selection assembly 108: the knife (or other cutting element), the electrosurgical energy, and the closure of the jaws 116a and 116b. Under each mode description 460, the chart 450 briefly describes the state of each of the components under column 455 for that particular mode.

For example, in the marching mode, the knife component is enabled after the jaws 116a and 116b are closed. Regarding the energy component, electrosurgical energy may be applied at the jaws 116a and 116b automatically upon jaw closure. That is, the user would not need to activate the energy button 122 or other kind of activation switch to apply energy to the jaws. Instead, the energy is immediately applied upon detection that the jaws 116a and 116b have closed. Regarding the state of the jaw closure, in marching mode, once the lever, e.g. trigger 109, is pulled and configured to be locked into the jaw closed state, electrosurgical energy is automatically activated and the knife may be enabled. For example, the trigger assembly 107 may be pulled half way toward the pistol grip 118 in order to close the jaws 116a and 116b. At this point, the energy would be automatically applied to the end effector 110 without any additional action required by the user. Then, the user may hold the trigger assembly 107 fully back toward the pistol grip 118 in order to fire the knife, all while energy is still being applied jaws 116a and 116b. While in the marching mode, the knife may be unlocked once the lever is locked into the jaw closed state.

As another example, in the cold cut mode, the knife component is enabled upon closure of the lever, e.g., trigger 109 pulled fully toward the pistol grip 118. That is, in this mode the cutting element may be unlocked after the lever is closed fully, and acted the end of the closure of the lever, the knife would also fire. Also in this mode, the energy would be disabled from use. Thus, in some cases, the energy button 122 may be depressed or locked, disabling use of the energy button 122 while in this mode. In general, the cold cut mode may represent a use of the surgical instrument 100 involving only activation of the cutting element without applying any energy. Regarding the jaw closure, in cold cut mode, the jaws 116a and 116b may close upon the trigger 109 being pulled, after which the knife component may be enabled for firing.

As another example, in the standard mode, the knife component is enabled only after energy is applied to the jaws 116a and 116b. However, as is typically standard, energy may be applied to the jaws 116a and 116b only after the jaws 116a and 116b are closed. Thus, in the standard mode, the jaws 116a and 116b would first need to be closed, then the energy would need to be manually applied by, e.g., pressing on the energy button 122, and then the knife may be unlocked to enable the knife fired. In contrast with the marching mode, as discussed herein, the standard mode does not automatically apply energy upon closure of the jaws 116a and 116b. Rather, the energy is merely enabled, and the user would apply the energy manually. In both cases, activating the cutting element would be possible only after energy is applied to the jaws 116a and 116b.

As a fourth example, in the seal only mode, the knife component is permanently locked. Only the energy is available for use in the seal only mode, where the energy may be applied once the jaws 116a and 116b are closed. Thus, as an example, the trigger 109 may be pulled towards the pistol grip 118, thereby closing the jaws 116a and 116b but not enabling use of the knife. Once the jaws 116a and 116b are closed, the user may then apply energy manually by, e.g., pressing the energy button 122. In general, the seal only mode only allows for energy to be applied to the surgical site through the jaws 116a and 116b, typically for sealing purposes, and prevents any inadvertent use of the knife. As shown through these four examples, aspects of the present disclosure include different modes that enable in the surgical instrument 100 the use of the energy only, the use of the knife only, and combinations of both in different configurations.

Still referring to FIG. 4B, chart 450 also provides a summary 465 of the sequence of actions that the surgical instrument 100 would be configured to perform while in each of the four example modes, e.g., the marching mode, the cold cut mode, the standard mode, and the seal only mode.

For example, at sequence 470, the surgical instrument 100 may receive an input by the user to switch to the marching mode through the turning of the knob 130 in the mode selection assembly 108 (FIG. 1, 4A). The surgical instrument 100 may then receive an input to close the jaws 116a and 116b, e.g., by the user pulling the trigger 109 toward the pistol grip 118. Upon detection or a trigger signaling that the jaws 116a and 116b are closed, the surgical instrument 100 may be configured to automatically activate the electrosurgical energy to be applied to the jaws 116a and 116b. After the energy is activated upon the jaw closure, the surgical instrument 100 may be configured to unlock the cutting element, e.g., the knife. Finally, the surgical instrument 100 may be configured to fire the knife upon receiving an input by the user, e.g., fully closing the trigger 109 toward the pistol grip 118.

As another example, at sequence 475, the surgical instrument 100 may receive an input by the user to switch to the cold cut mode through the turning of the knob 130 in the mode selection assembly 108. The surgical instrument 100 may then receive an input to pull the trigger 109 toward the pistol grip 118, thereby closing the jaws 116a and 116b. Upon detection or a trigger signaling that the jaws 116a and 116b are closed, the surgical instrument 100 may be configured to unlock the cutting element. Finally, the surgical instrument 100 may be configured to fire the knife upon receiving an input by the user, e.g., fully closing the trigger 109 toward the pistol grip 118. Notice here that in the cold cut mode, the sequence of actions 475 does not include any application of energy being applied to the jaws 116a and 116b.

As a third example, at sequence 480, the surgical instrument 100 may receive an input by the user to switch to the standard mode through the turning of the knob 130 in the mode selection assembly 108. The surgical instrument 100 may then receive an input to close the jaws 116a and 116b, such as by the user pulling the trigger 109 towards the pistol grip 118. Upon detection or a trigger signaling that the jaws 116a and 116b are closed, the surgical instrument 100 may be configured to enable application of the energy to the jaws 116a and 116b. The surgical instrument 100 may then receive an input to apply the energy to the jaws 116a and 116b, e.g., by the user pushing the energy button 122 to activate the energy. After detecting that the energy is applied to the jaws 116a and 116b, the surgical instrument 100 may be configured to unlock the cutting element. Finally, the surgical instrument 100 may be configured to fire the knife upon receiving an input by the user, e.g., fully closing the trigger 109 toward the pistol grip 118.

As a fourth example, at sequence 485, the surgical instrument 100 may receive an input by the user to switch to the seal only mode through the turning of the knob 130 and the mode selection assembly 108. The surgical instrument 100 may then receive an input to close the jaws 116a and 116b, such as by the user pulling the trigger 109 toward the pistol grip 118. The surgical instrument 100 may be configured to detect that the jaws are closed, at which point the surgical instrument 100 may be configured to enable application of electrosurgical energy. The surgical instrument 100 may then receive an input to apply the energy to the jaws 116a and 116b, such as by the user pressing the energy button 122. Notice here that the knife is not activated at any point during the seal only mode action sequence 485. Only the energy is available to be applied after the jaws 116a and 116b are closed.

Cutting Element Control Examples

FIGS. 5A-9C provide various examples for locking and unlocking the cutting element of the surgical instrument 100, according to some embodiments. The example mechanisms provided herein may serve as some examples describing how the cutting element, e.g., the knife, may be unlocked, within the context of the various action sequences for operating the various modes of the surgical instrument 100, e.g., through selection of the mode selection assembly 108 (see FIGS. 4A-4B).

Referring to FIG. 5A, illustration 500 shows various mechanical and electrical components within the surgical instrument, such as surgical instrument 100, comprising a mechanical system with an electric motor for locking and unlocking use of a cutting element of the surgical instrument 100, according to some embodiments. Here, a portion of the trigger 109 is shown, fixedly coupled to trigger plate 124, in this case implemented in a different design than what is shown in FIGS. 1-3. The trigger 109 and the trigger plate 124 may together rotate via hinge 126. Also fixedly coupled to the trigger plate 124 may be the firing plate 128, not shown, comprising gear teeth 131 that are connected to the system of pinion gears 133 and 134, as shown. Thus, when fully rotated in the clockwise direction by pulling on the trigger 109, as previously described, the trigger plate 124 may be configured to rotate the firing plate 128, which in turn causes rotations of the gears 133 and 134, driving the rack 136 to cause firing of the knife in the distal direction through the shaft 112. Also shown is energy button 122 coupled to various mechanical components that allow for the energy button 122 to be continually pressed and depressed. The energy button 122 may also be coupled to various electrical components that drive energy to the end effector 110 of the surgical instrument (FIG. 1).

Also shown is the tissue sealer mode selection assembly 108, including the mode selection knob 130 and the pointer 405 to indicate which mode is selected. The mode selection assembly 108 may be electrically coupled to the energy button 122, such that, in certain modes, the energy button 122 may deliver electrosurgical energy to the end effector 110 when pressed. In addition, the mode selection assembly 108 may be electrically coupled to an electric motor 510. Electric motor 510 may be configured to drive a mechanical lockout switch 505, as shown. In illustration 500, the lockout switch 505 is touching the trigger plate 124 such that the trigger plate 124 cannot rotate any further in the counter-clockwise direction. Since the trigger plate 124 is fixedly coupled to the trigger 109, the trigger 109 also cannot be pulled back any further in this current configuration. As shown, the lockout switch 505 may currently be in a lockout position, preventing the user from mechanically driving any operation of the knife.

Figure 5B:
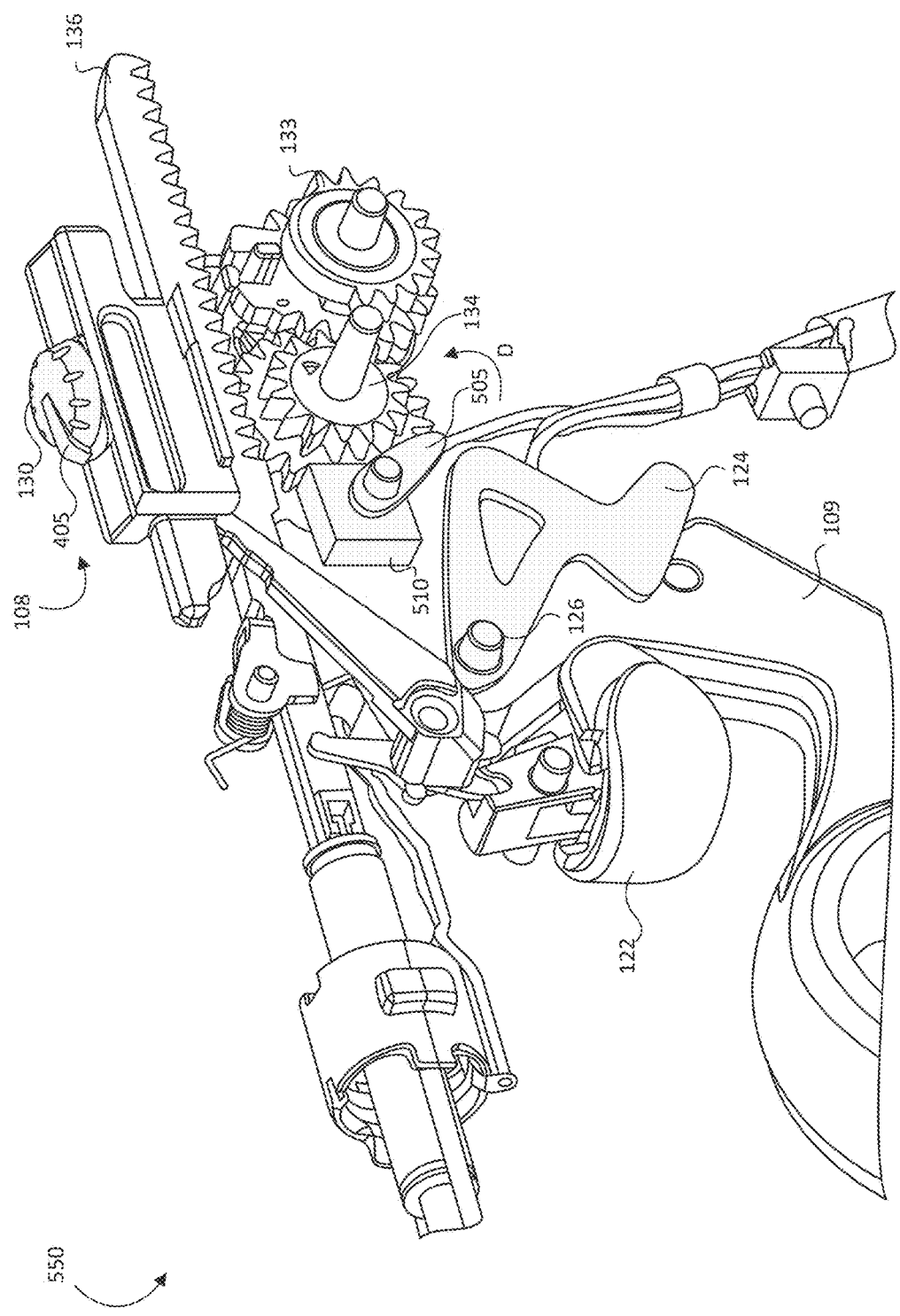
FIG. 5B shows the mechanical lockout system with electric motor in an unlocked state, according to some embodiments.

Referring to FIG. 5B, illustration 550 shows the mechanical lockout system with electric motor in an unlocked state, according to some embodiments. That is, in certain modes selected via the mode selection knob 130, the mode selection assembly 108 may be configured to apply electrical current to the motor 510 to rotate the lockout switch 505 in the direction "D," as shown. The rotation of the lockout switch 505 allows the trigger plate 124 to continue rotating in the counterclockwise direction via hinge 126. Thus, the motor 510 is configured to unlock firing of the knife by rotating away the lockout switch 505 to allow the trigger plate 124 to fully rotate. In some embodiments, the steps in chart 450 describing the knife to be unlocked may include performing this unlocking technique as described.

Figure 6A:
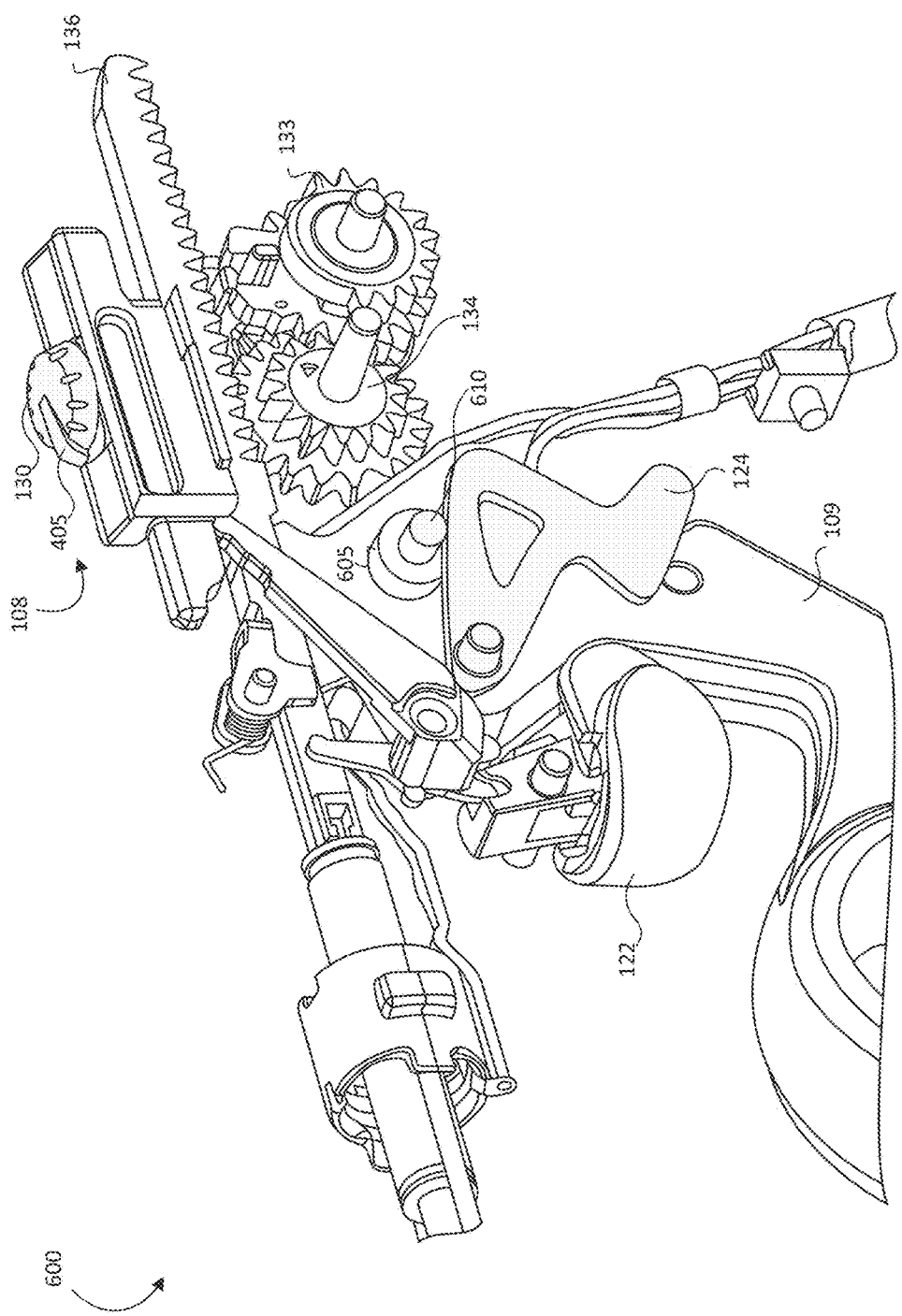
FIG. 6A shows another example implementation for locking and unlocking the cutting element of the surgical instrument, this time using an electromechanical solenoid switch, according to some embodiments.

Referring to FIG. 6A, illustration 600 shows another example implementation for locking and unlocking the cutting element of the surgical instrument 100, this time using an electromechanical solenoid switch 605, according to some embodiments. As shown, the various components of the surgical instrument 100 may be consistent with the descriptions in illustration 500 (FIG. 5A), except here, instead of the electric motor with the mechanical switch, an electromechanical solenoid switch 605 is electrically coupled to the tissue sealer mode selection assembly 108 and is used to physically prevent complete rotation of the trigger plate 124. In this example, the solenoid switch 605 includes a pin 610 that is currently engaged with the trigger plate 124. The solenoid switch 605 may be electrically coupled to the mode selection assembly 108, and may be controlled by the change in modes through the mode selection assembly 108. For example, switching modes via the knob 130 may change settings in a controller circuit, not shown, connected to the solenoid switch 605. The controller circuit may be configured to change the inductance of an electromagnetically inductive coil wound around the pin 610. Thus, changes in the inductance of the coil will drive the pin 610 back-and-forth within the solenoid switch 605.

Figure 6B:
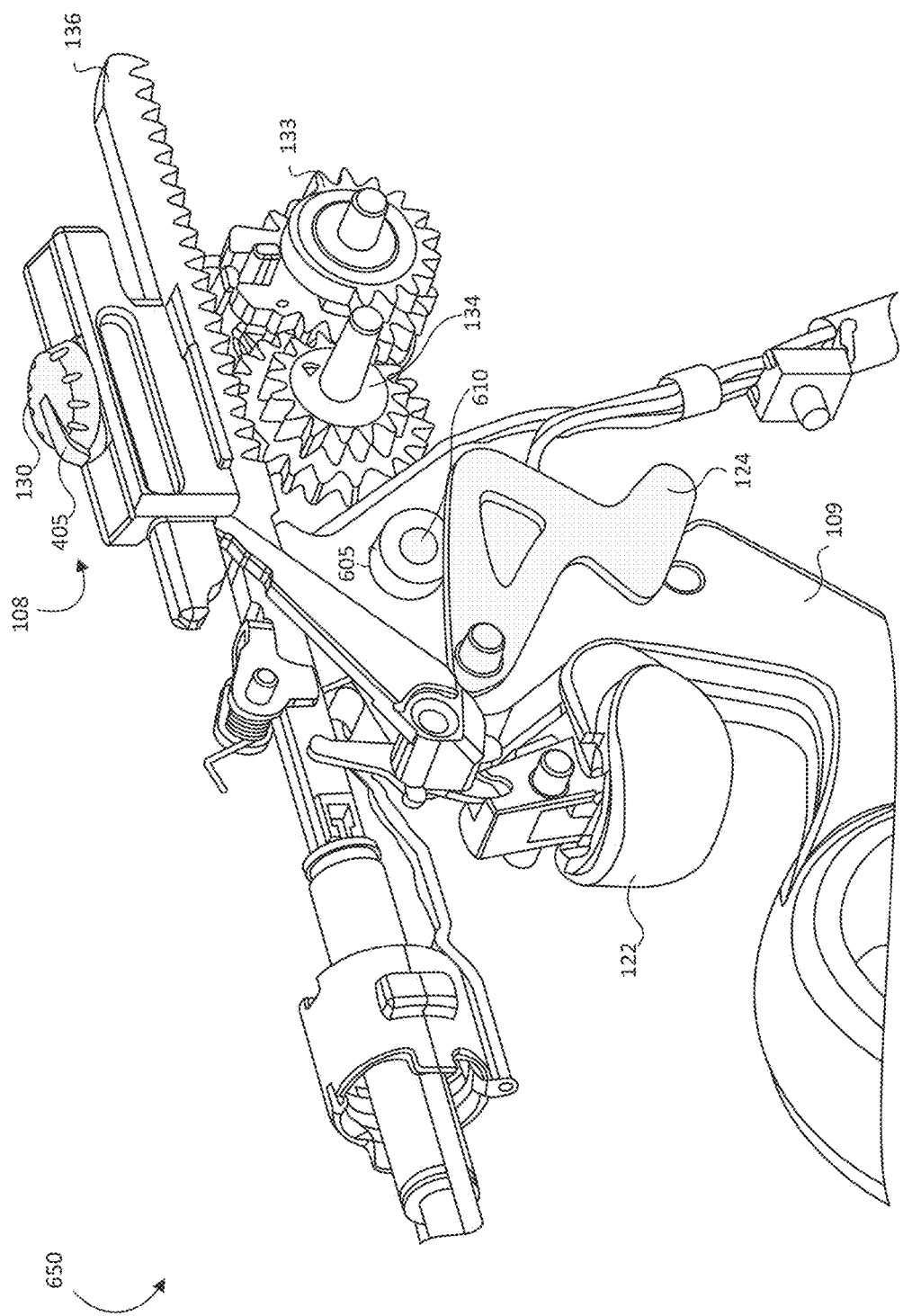
FIG. 6B shows the solenoid switch in an unlocked position, according to some embodiments.

Referring to FIG. 6B, illustration 650 shows the solenoid switch 605 in an unlocked position, according to some embodiments. Here, the pin 610 is shown to be retracted into the solenoid switch 605. This may be achieved by altering the coil's inductance via the controller circuit, such that the pin will be driven into the solenoid switch in order to increase the coil's inductance, following Faraday's law of induction. Once the pin 610 is fully retracted into the solenoid switch 605, the trigger plate 124 may safely rotate across the solenoid switch 605, unimpeded. This may allow full rotation of the trigger plate 124 and the trigger 109, thereby rotating the firing plate 128 two ultimately cause the rack 136 to fire the knife. By using a solenoid switch 605, very quick reaction times between locking and unlocking the trigger plate 124 may be achieved, due to the near instantaneous nature of the pin 610 reactions to modifying the inductance of the coil.

Figure 7A:
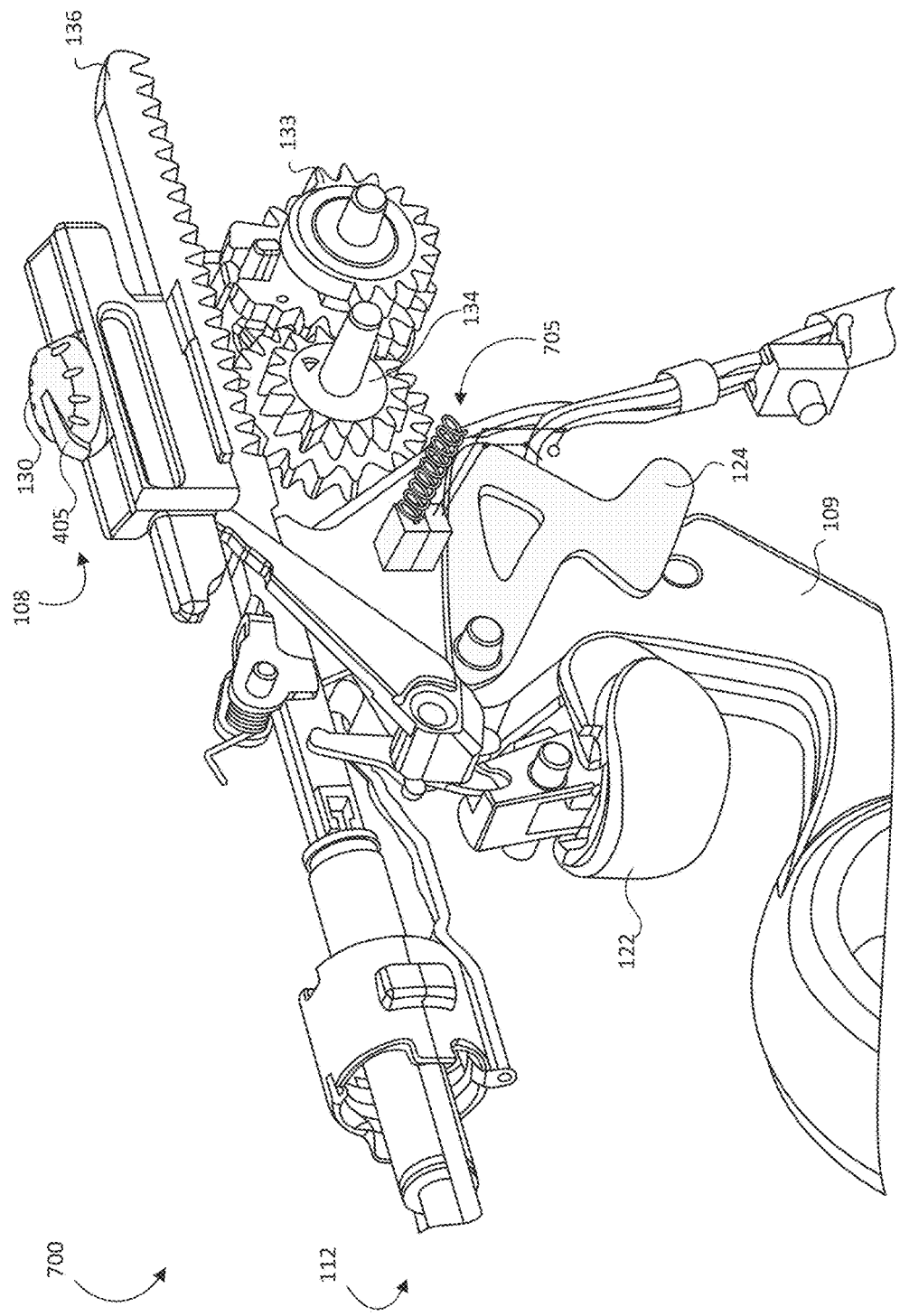
FIG. 7A shows yet another example for locking and unlocking the cutting element of the surgical instrument, this time using an electromechanical spring-circuit system involving a nitinol wire, according to some embodiments.

Referring to FIG. 7A, illustration 700 shows yet another example for locking and unlocking the cutting element of the surgical instrument 100, this time using an electromechanical spring-circuit system involving a nitinol wire, according to some embodiments. In illustration 700, the various electrical and mechanical components of the surgical instrument 100 may be consistent with the components described in illustration 500 (FIG. 5A), except here, the lockout mechanism for the cutting element includes an electromechanical spring-circuit system 705 involving a nitinol wire. As shown, the spring-circuit system 705 is resting in the natural state that locks trigger plate 124 from fully rotating, thereby preventing the knife from firing. The spring of the spring circuit system 705 is in its natural, uncoiled state, which causes a block to prevent the trigger plate 124 from fully rotating. The mechanics of the spring circuit system 705 will be described in the following figure.

Figure 7B:
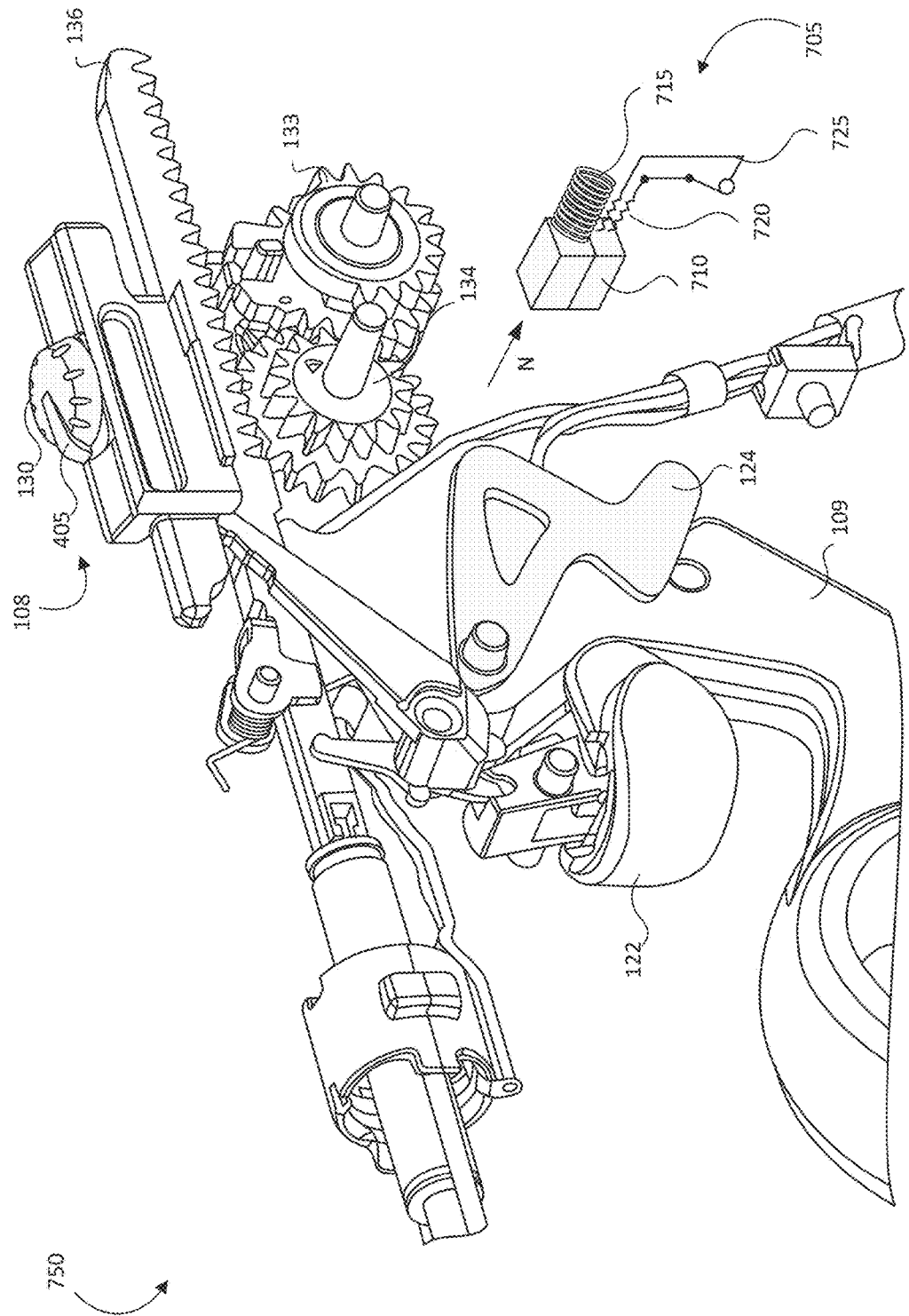
FIG. 7B shows the surgical instrument with the electromechanical spring circuit system 705 in an unlocked state, according to some embodiments.

Referring to FIG. 7B, illustration 750 shows the surgical instrument 100 with the electromechanical spring circuit system 705 in an unlocked state, according to some embodiments. The blocks 710 used to prevent the trigger plate 124 from fully rotating has been pulled back in the direction "N," and is shown to be pulled out far away from the rest of the surgical instrument 100 in an exaggerated state for clarity. As shown, the spring circuit system several five includes the blocks 710 attached to a spring 715 and a nitinol wire 720. The nitinol wire may be attached to other electrical circuitry 725 to form a closed circuit, which is electrically coupled to the mode selection assembly 108, using circuitry not shown. The end of the spring 715 distal to the block 710 may be closed against the outer casing of the surgical instrument 100, for example. In addition, the circuitry connecting the nitinol wire 722 the mode selection assembly 108 may run along the outer casing of the surgical instrument 100, not shown.

Nitinol wire exhibits shape memory and super elasticity properties that allow the nitinol wire 720 to undergo deformation at room temperature and then recover its original, un-deformed shape upon heating above a threshold transformation temperature. In this case, the "original" shape of the nitinol wire 720 is the crinkled, zigzag shape that allows for the block 710 to be pulled back in the unlocked state, as shown in illustration 750. This crinkled shape may be first "fixed" into the nitinol wire 720 by shaping the nitinol wire 720 at a very high temperature, such as around 500° C.

When at room temperature, the nitinol wire 720 may exhibit elastic properties that allow it to be stretched and deformed through various forces. In this case, the spring 715 will exhibit a natural force of uncoiling as far out as it can. Thus, at room temperature, the spring 715 will push the block 710 toward the trigger plate 124, allowing the spring circuit system 705 to be in a locked state. Because of its elastic nature, the nitinol wire 720 will be stretched out due to being connected to the block 710 (see FIG. 7A).

The spring circuit system 705 may pull back the block 710 to unlock the plate 124 by applying a current through the circuitry 725 to the nitinol wire 720. The current applied to the circuitry 725 may occur when the mode selection assembly 108 is selected to be in a mode that unlocks cutting element. The current applied to the nitinol wire 720 may be designed such that the nitinol wire 720 will be heated to a specific transformation temperature. Due to its shape memory properties, when heated to the transformation temperature, the nitinol wire 720 will revert back to its "original" shape, which in this case is the crinkled, zigzag shape as described previously. Thus, the current applied to the nitinol wire 720 causes the nitinol wire 720 to act like a spring, pulling back the block 710 in order to conform back to its "original," crinkled shape. The spring circuit system 705 is designed such that force that the nitinol wire 720 exerts to revert back to its wrinkled shape sufficiently overcomes the natural force of the spring 715 to want to be uncoiled.

This unlocking and locking process can be repeated continuously upon applying sufficient current to the nitinol wire 720 or not. For example, the spring circuit system 705 may be configured to again lock trigger plate 724 by disabling any current from being applied to the nitinol wire 720. The temperature of the nitinol wire 720 would then drop, causing the nitinol wire 722 be deformed by other forces, which would allow the spring 715 to uncoiled again and pushed the block 710 back into place.

Referring to FIG. 8A, illustration 800 shows another example variation of the spring circuit system described in illustrations 700 and 750, according to some embodiments. Here, the spring circuit system of illustration 800 may be arranged with the nitinol wire 720' wrapped around a series of pulleys 825. The nitinol wire 720' is coupled to a locking switch 805 that locks to a latch 820 connected to a lever 815. While shown as a long bar, the lever 815 may be functionally equivalent to other components in the surgical instrument 100, such as trigger plate 124. However, in this case, when the locking switch 805 is in the locking position as shown in illustration 800, the lever 815 is prevented from sliding, which may be used to prevent the knife from firing through the shaft 112 (FIG. 7A), for example.

The spring circuit system of illustration 800 is also operated through the opposing forces of the spring 715' and the nitinol wire 720', when a current is applied at the circuit box 830. For example, when no current is applied, the spring 715' is configured to naturally uncoiled so as to push up the locking switch 805, to block the latch 820 from sliding past the locking switch 805, as shown. Here, the locking switch 805 is configured to give it via the hinge 810.

Figure 8B:
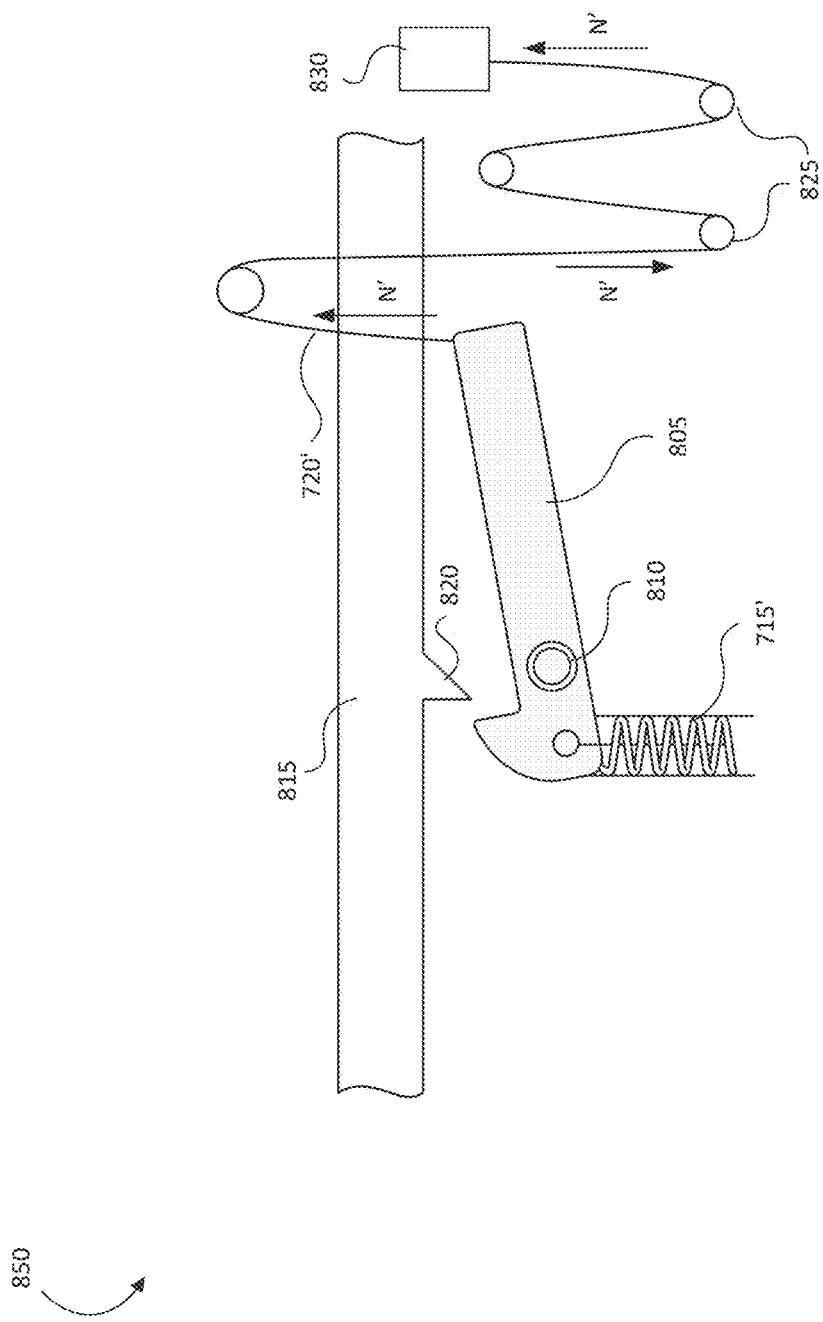
FIG. 8B shows the surgical instrument with the electromechanical spring circuit system in an unlocked state, according to some embodiments.

Referring to FIG. 8B, illustration 850 shows the alternate spring circuit system in an unlocked state, according to some embodiments. That is, when electrical current is applied to the circuit box 830, the nitinol wire 720' is heated sufficiently to revert back to its "original" shape, which in this case includes at least a portion of the nitinol wire 720' crinkled up in a zigzag shape. This causes the nitinol wire 720' to move in the direction of N', as shown. In some embodiments, the wheels 825 help to create a pulley system that's may provide additional leverage for the nitinol wire 720' to pull up the locking switch 805. In addition, this series of wheels 825 may be configured to enable a pulley system that is positioned laterally to the locking switch 805, rather than needing to be positioned above or below it. Thus, as the nitinol wire 720' pulls up on the and of the locking switch 805 distal to the spring 715'. With the hinge 810 as a fulcrum, the spring 715' will also be sufficiently depressed, thereby allowing the latch 822 be unblocked by the locking switch 805.

Referring to FIG. 9A, illustration 900 shows another example of a locking system comprised of only mechanical components, according to some embodiments. Here, a rotating dial 902 may include a C-shaped groove 904 that is carefully cut into the dial 902 such that, when the dial 902 is rotated, the beam 906 attached to the groove 904 is configured to slide laterally between the center of the dial 902 and its outside edge, as shown. The dial 902 may be mechanically coupled to the knob 130 of the mode selection assembly 108 (see e.g., FIG. 5A) such that rotating the knob 130 causes the dial 902 to rotate accordingly.

At the end of the beam 906 distal to the dial 902 may include a locking mechanism comprised of a locking block 908 attached to a spring 910. The beam 906 may be fixedly coupled to the locking block 908. The end of the spring 910 distal to the locking block 908 may be attached to the inside of an outer casing of the surgical instrument 100, for example. Also shown is a trigger 912 coupled to the locking block 908, and a switch 914 that may be configured to operate in electrical component of the surgical instrument 100 when flipped. A lever or bar, such as the trigger plate 124, is shown as an example of the component that is intended to be locked by the locking block 908.

In illustration 900, the dial 902 has been turned such that the beam 906 is placed on the outer edge of the dial 902, due to its position in the groove 904, as shown. Being on the outer edge, in this case, causes the beam 906 to force the locking block 908 toward the right, which also depresses the spring 910, as shown. In this position, the locking block 908 is moved out beyond the trigger plate 124 in an unlocked state. As shown, this allows the trigger plate 124 to slide or rotate or otherwise complete its full range of motion.

Referring to FIG. 9B, illustration 930 shows a partial movement of the mechanical lockout mechanism for locking the trigger plate 124, according to some embodiments. As shown, the dial 902 may be rotated in a clockwise direction according to the rotational direction "M." As shown, due to the C-shaped nature of the groove 904, the beam 906 is moved laterally toward the center of the dial 902. Because the beam 906 is forced to move laterally toward the left, this relaxes the position of the beam 906 and allows the spring 910 to uncoil, thereby moving the locking block 908 to the left.

Referring to FIG. 9C, illustration 960 shows the mechanical lockout mechanism in its fully locked state, according to some embodiments. Here, the dial 902 is rotated fully in the clockwise direction "M'." The beam 906 is now positioned closest to the center of the dial 902 based on the shape of the groove 904. This allows the beam 906 to be relaxed fully in the lateral direction to the left, thereby allowing the spring 910 to fully uncoil, as shown. Thus, the block 908 has completely blocked the trigger plate 124 from completing its rotation or other preconfigured movement. In addition, in some embodiments, the trigger 912 would have touched the switch 914 as the locking block 908 moved in the lateral direction to the left. Flicking the switch 914 via the trigger 912 may cause an additional locking or unlocking activation to occur, such as electrically enabling the use of electrosurgical energy to be applied to the end effector 110 (see FIG. 1). Conversely, as the dial 902 is rotated in the counterclockwise direction, the sequence described herein is reversed, including the trigger 912 flicking the switch 914 in the opposite direction. This may cause the reverse action as described previously.

Referring to FIGS. 10A-10I, various illustrations are shown providing a summary of example locked and unlocked states of various example implementations of the lockout mechanism for the cutting element, according to some embodiments. Referring to FIG. 10A, illustration 1000 provides a simplified illustration of the locked state of the trigger plate 124 using the electric motor and mechanical lockout mechanism described in FIG. 5A. As shown, the lockout mechanism 505 is rotated to press against the trigger plate, such that the trigger plate cannot fully rotate while in the locket state. In FIG. 10B, illustration 1005 shows the electric motor having rotated the mechanical lockout mechanism 505 to the unlocked state, as described in FIG. 5B. Here, the lockout mechanism 505 has rotated such that the trigger plate can continue to rotate in the counterclockwise direction that it was previous prevented from doing while in the locked stated.

Referring to FIG. 10C, illustration 1010 provides a simplified illustration of the locked state of the trigger plate 124 using the solenoid switch lockout mechanism described in FIG. 6A. As shown, the solenoid switch 605 causes the pin 610 to protrude beyond the solenoid when the inductance of the solenoid is configured in a particular way, consistent with the descriptions in FIG. 6A. The protruding pin 610 prevents the trigger plate from rotating completely, thereby preventing firing of the knife in the surgical instrument 100. In FIG. 10D, illustration 1015 shows the solenoid switch lockout mechanism in the unlocked state, where the pin 610 is now retracted into the solenoid switch 605. This allows the trigger plate to swing fully and perform its full function.

Referring to FIG. 10E, illustration 1020 provides a simplified illustration of the locked state of the trigger plate 124 using the spring-circuit lockout mechanism described in FIG. 7A. As shown, a spring pushes out a block to prevent movement of the trigger plate when the circuit is open, consistent with the descriptions in FIG. 7A. The block prevents the trigger plate from rotating completely, thereby preventing firing of the knife in the surgical instrument 100. The circuit is coupled to at least one nitinol wire that is configured to change shape when heated to a threshold temperature. When not at the threshold temperature, the nitinol wires may be manipulated through other forces, such as the force of the spring. In FIG. 10F, the circuit is closed and energy is applied to the nitinol wires. When the wires are sufficiently heated, the nitinol wires revert back to their "memory" shapes, as shown. These forces counteract the force of the spring, thereby pulling back the block to allow the trigger plate to swing fully, consistent with the descriptions in FIG. 7B.

Referring to FIG. 10G, illustration 1030 provides an illustration of one setting of the mode selection assembly using a purely mechanical implementation, according to some embodiments and consistent with the descriptions in FIG. 9A. As shown, the dial 902 may be rotated such that the mechanical lockout mechanism allows the trigger plate to swing fully, but the switch to activate the electrosurgical energy has not yet been triggered. Thus, the mode selection assembly is presently configured for the "cold cut" mode in illustration 1030. In FIG. 10H, illustration 1035 shows the dial 902 rotated further in the counterclockwise direction. This may represent an example of the "standard" mode of the mode selection assembly, because the switch to activate the energy may be toggled and the trigger plate may be allowed to swing fully as well. As shown, the switch may be 914 may be tripped by the trigger 912, causing the energy to be activated. In FIG. 10I, illustration 1040 shows the dial 902 rotated further in the counterclockwise direction. This may represent an example of the "seal only" mode of the mode selection assembly, because the switch 914 to activate the energy may be toggled, but the trigger plate may be blocked to prevent full operation of the knife from firing.

Referring to FIG. 11A, illustration 1100 provides an example block diagram for performing electrical processes described in the present disclosures herein, according to some embodiments. One or more inputs may be provided to a microprocessor 1105. The microprocessor 1105 may be part of a printed circuit board built into the surgical instrument 100, for example. Example inputs may include changing to a particular mode using the mode selection assembly 108, the pressing of the energy button 122, and the closing of the jaws 116a and 116b by the trigger assembly 107. Based on the inputs to the microprocessor 1105, one or more outputs may be provided. Example outputs can include activating the electrosurgical energy to be applied to the jaws 116a and 116b, enabling or disabling the use of electrosurgical energy when the energy button 122 is pressed, and applying electricity to enable or disable a lockout mechanism for the cutting element, in some cases.

Referring to FIG. 11B, illustration 1150 provides a block diagram of the various elements of the microprocessor 1105, according to some embodiments. For example, the microprocessor 1105 may include an instruction processing unit 1107, an arithmetic unit 1109, and a memory 1106. The memory circuit 1106 may comprise volatile and non-volatile storage media. The instruction processing unit 1107 may be configured to receive instructions from the memory circuit 1106.

In certain instances, one or more of the switches described by the present disclosure such as, for example, the energy button 122 and the mode selection assembly 108 may comprise mechanical switches, electro-mechanical switches, and/or solid state switches. In certain instances, the energy button 122 or the mode selection assembly 108 may comprise open, inactive, and/or non-conductive positions, states, and/or configurations. In certain instances, the energy button 122 or the mode selection assembly 108 may include active, and/or conductive positions, states and/or configurations. In certain instances, one or more of the switches of the present disclosure such as, for example, the energy button 122 or the mode selection assembly 108 can be transitioned from the open, inactive, and/or non-conductive positions, states, and/or configurations to the closed, active, and/or conductive positions, states and/or configurations to close and/or activate one or more circuits associated with such switches, for example.

In some embodiments, a circuit for controlling the electrical processes of the surgical instrument 100 may comprise a finite state machine comprising a combinational logic circuit. For example, the circuit may comprise a finite state machine comprising a sequential logic circuit. The sequential logic circuit may comprise the combinational logic circuit and at least one memory circuit, for example. The at least one memory circuit can store a current state of the finite state machine. The sequential logic circuit or the combinational logic circuit can be configured to cause the finite state machine to detect activation of the energy button 122, or a change in the mode selection of the mode selection assembly 108, determine if a change has been detected, and transition to another state in the finite state machine based on the combinational logic consistent with the methods described herein, including, for example, the methods described in FIG. 4B. In certain instances, the sequential logic circuit may be synchronous or asynchronous. In other embodiment, the circuit 1100 may comprise a combination of the microprocessor 1105 and the finite state machine to perform the various methods described herein.

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a general purpose processor or application specific processor. The embodiments, however, are not limited in this context.

The functions of the various functional elements, logical blocks, modules, and circuits elements described in connection with the embodiments disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures and the like that perform particular tasks or implement particular abstract data types. An implementation of the software, control modules, logic, and/or logic modules and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

It is worthy to note that some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, and application program interface (API), exchanging messages, and so forth.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

The invention claimed is:

1. A surgical instrument, comprising:
    an end effector comprising:
        a movable jaw;
        at least one electrode; and
        a cutting element slidably movable within the end effector;
    a handle assembly comprising:
        an energy button configured to deliver energy to the at least one electrode;
        a trigger plate operably coupled to a jaw closure mechanism, the trigger plate configured to close the movable jaw;
        a firing plate operably coupled to a cutting element drive mechanism, the firing plate configured to drive the cutting element independently of the jaw closure mechanism;

a lockout mechanism coupled to the cutting element drive mechanism and, in a locked state, is configured to disable movement of the cutting element; and a mode selection assembly coupled to the energy button and the lockout mechanism, the mode selection assembly configured to select between different modes.

2. The surgical instrument of claim 1, wherein:
in one mode, energy is enabled to be delivered to the at least one electrode after the movable jaw is closed; and
in another mode, energy is disabled from being delivered to the at least one electrode.

3. The surgical instrument of claim 1, wherein:
in a first mode, the cutting element is enabled to move after the energy is applied by transitioning the cutting element lockout mechanism to an unlocked state; and
in a second mode, the cutting element is disabled from moving after the movable jaw is closed by transitioning the lockout mechanism to the unlocked state.

4. The surgical instrument of claim 1, wherein in any mode, the firing plate is enabled to drive the cutting element only after energy is delivered to the at least one electrode and after the movable jaw is closed.

5. A end effector comprising:
an end effector comprising:
a movable jaw;
at least one electrode; and
a cutting element slidably movable within the end effector;
a handle assembly comprising:
an energy button configured to deliver energy to the at least one electrode;
a trigger plate operably coupled to a jaw closure mechanism, the trigger plate configured to close the movable jaw;
a firing plate operably coupled to a cutting element drive mechanism, the firing plate configured to drive the cutting element independently of the jaw closure mechanism;
a cutting element lockout mechanism coupled to the cutting element drive mechanism and configured to disable movement of the cutting element; and
a mode selection assembly coupled to the energy button and the cutting element lockout mechanism, the mode selection assembly comprising a knob configured to rotate between a first mode and a second mode, wherein:
in the first mode, the mode selection assembly is configured to:
enable the energy to be delivered to the at least one electrode after the movable jaw is closed;
enable movement of the cutting element after the energy is applied by transitioning the cutting element lockout mechanism to an unlocked state; and
enable the firing plate to drive the cutting element; and
in the second mode, the mode selection assembly is configured to:
disable the energy from being delivered to the at least one electrode;
enable movement of the cutting element after the movable jaw is closed by transitioning the cutting element lockout mechanism to the unlocked state; and
enable the firing plate to drive the cutting element.

6. The surgical instrument of claim 5, wherein the mode selection assembly further comprises a third mode, wherein the knob is configured to rotate between the first, second, and third modes, and wherein:
in the third mode, the mode selection assembly is further configured to:
enable the energy to be delivered to the at least one electrode after the movable jaw is closed; and
disable movement of the cutting element by transitioning the cutting element lockout mechanism to a locked state.

7. The surgical instrument of claim 5, wherein the mode selection assembly further comprises a fourth mode, wherein the knob is configured to rotate between the first, second, and fourth modes, and wherein:
in the fourth mode, the mode selection assembly is further configured to:
automatically deliver the energy to the at least one electrode after the movable jaw is closed;
enable movement of the cutting element after the energy is delivered by transitioning the cutting element lockout mechanism to the unlocked state; and
enable the firing plate to drive the cutting element.

8. The surgical instrument of claim 5, wherein the cutting element lockout mechanism comprises:
an electric motor coupled to the mode selection assembly; and
a mechanical switch coupled to the electric motor and configured to rotate between a locked state and the unlocked state;
wherein:
a first electric signal applied to the electric motor causes the mechanical switch to rotate to the locked state and prevent complete movement of the trigger plate; and
a second electric signal applied to the electric motor causes the mechanical switch to rotate to the unlocked state and allow complete movement of the trigger plate.

9. The surgical instrument of claim 5, wherein the cutting element lockout mechanism comprises:
a solenoid coupled to the mode selection assembly; and
a pin coupled to the solenoid and configured to transition between a locked state and the unlocked state;
wherein:
a first electric signal applied to the solenoid causes the pin to protrude outside the solenoid in the locked state and prevent complete movement of the trigger plate; and
a second electric signal applied to the solenoid causes the pin to retract inside the solenoid in the unlocked state and allow complete movement of the trigger plate.

10. The surgical instrument of claim 5, wherein the cutting element lockout mechanism comprises:
a control circuit electrically coupled to the mode selection assembly;
a wire comprising shape memory and elasticity characteristics and coupled to the control circuit, the wire configured to change shape when a current is applied to it by the control circuit due to the shape memory and elasticity characteristics;
a lockout block coupled to the wire; and
a spring coupled to the lockout block, wherein the spring is positioned parallel to the wire.

11. The surgical instrument of claim 10, wherein:
an electric signal applied to the control circuit causes the wire to contract and pull the lockout block away from the trigger plate to allow complete movement of the trigger plate; and
the electric signal not applied to the control circuit causes the wire to relax and the spring to push the lockout block toward the trigger plate to prevent complete movement of the trigger plate.

12. The surgical instrument of claim 5, wherein the cutting element lockout mechanism comprises:
a dial coupled to the mode selection assembly and configured to rotate coaxially with the knob, the dial comprising a curved groove;
a beam comprising a proximal end coupled to a hinge in the curved groove and configured to slide within the curved groove upon rotation of the dial;
a lockout block coupled to the beam; and
a spring coupled to the lockout block.

13. The surgical instrument of claim 12, wherein:
a first rotation in a first direction applied to the dial causes the lockout block to protrude beyond the trigger plate in a locked state and prevent complete movement of the trigger plate; and
a second rotation in a second direction applied to the dial causes the lockout block to retract away from the trigger plate in the unlocked state and allow complete movement of the trigger plate.

14. A surgical instrument, comprising:
an end effector comprising:
 a movable jaw;
 at least one electrode; and
 a cutting element slidably movable within the end effector;
a handle assembly comprising:
 an energy button configured to deliver energy to the at least one electrode located in the end effector;
 a trigger plate operably coupled to a jaw closure mechanism, the trigger plate configured to close the movable jaw;
 a firing plate operably coupled to a cutting element drive mechanism, the firing plate configured to drive the cutting element independently of the jaw closure mechanism;
a cutting element lockout mechanism coupled to the cutting element drive mechanism, wherein the cutting element is configured to move between a locked state and an unlocked state to:
 disable movement of the cutting element in the locked state; and
 enable movement of the cutting element in the unlocked state; and
a mode selection assembly coupled to the energy button and the cutting element lockout mechanism, the mode selection assembly comprising a knob configured to rotate between a first mode, a second mode, a third mode, and a fourth mode, wherein:
 in the first mode, the mode selection assembly is configured to:
  enable the energy to be delivered to the at least one electrode after the movable jaw is closed;
  enable movement of the cutting element after the energy is applied by transitioning the cutting element lockout mechanism to the unlocked state; and
  enable the firing plate to drive the cutting element;
 in the second mode, the mode selection assembly is configured to:
  disable the energy from being delivered to the at least one electrode;
  enable movement of the cutting element after the movable jaw is closed by transitioning the cutting element lockout mechanism to the unlocked state; and
  enable the firing plate to drive the cutting element;
 in the third mode, the mode selection assembly is configured to:
  enable the energy to be delivered to the at least one electrode after the movable jaw is closed; and
  disable movement of the cutting element by transitioning the cutting element lockout mechanism to the locked state; and
 in the fourth mode, the mode selection assembly is configured to:
  automatically deliver the energy to the at least one electrode after the movable jaw is closed;
  enable movement of the cutting element after the energy is delivered by transitioning the cutting element lockout mechanism to the unlocked state; and
  enable the firing plate to drive the cutting element.

15. The surgical instrument of claim 14, wherein the cutting element lockout mechanism comprises:
an electric motor coupled to the mode selection assembly; and
a mechanical switch coupled to the electric motor and configured to rotate and move the cutting element between the locked state and the unlocked state;
wherein:
a first electric signal applied to the electric motor causes the mechanical switch to rotate to the locked state and prevent complete movement of the trigger plate; and
a second electric signal applied to the electric motor causes the mechanical switch to rotate to the unlocked state and allow complete movement of the trigger plate.

16. The surgical instrument of claim 14, wherein the cutting element lockout mechanism comprises:
a solenoid coupled to the mode selection assembly; and
a pin coupled to the solenoid and configured to transition between the locked state and the unlocked state;
wherein:
a first electric signal applied to the solenoid causes the pin to protrude outside the solenoid in the locked state and prevent complete movement of the trigger plate; and
a second electric signal applied to the solenoid causes the pin to retract inside the solenoid in the unlocked state and allow complete movement of the trigger plate.

17. The surgical instrument of claim 14, wherein the cutting element lockout mechanism comprises:
a control circuit electrically coupled to the mode selection assembly;
a wire comprising shape memory and elasticity characteristics and coupled to the control circuit, the wire configured to change shape when a current is applied to it by the control circuit due to the shape memory and elasticity characteristics;
a lockout block coupled to the wire; and
a spring coupled to the lockout block, wherein the spring is positioned parallel to the wire.

18. The surgical instrument of claim 17, wherein:
an electric signal applied to the control circuit causes the wire to contract and pull the lockout block away from the trigger plate to allow for complete movement of the trigger plate; and
the electric signal not applied to the control circuit causes the wire to relax and the spring to push the lockout block toward the trigger plate to prevent complete movement of the trigger plate.

19. The surgical instrument of claim 14, wherein the cutting element lockout mechanism comprises:

a dial coupled to the mode selection assembly and configured to rotate coaxially with the knob, the dial comprising a curved groove;
a beam comprising a proximal end coupled to a hinge in the curved groove and configured to slide within the curved groove upon rotation of the dial;
a lockout block coupled to the beam; and
a spring coupled to the lockout block.

20. The surgical instrument of claim 19, wherein:
a first rotation in a first direction applied to the dial causes the lockout block to protrude beyond the trigger plate in the locked state and prevent complete movement of the trigger plate; and
a second rotation in a second direction applied to the dial causes the lockout block to retract away from the trigger plate in the unlocked state and allow complete movement of the trigger plate.

* * * * *